US009867556B2

(12) United States Patent
Balachandran et al.

(10) Patent No.: US 9,867,556 B2
(45) Date of Patent: Jan. 16, 2018

(54) SYSTEM AND METHOD FOR ASSESSING DIMENSIONS AND ECCENTRICITY OF VALVE ANNULUS FOR TRANS-CATHETER VALVE IMPLANTATION

(71) Applicant: St. Jude Medical, Cardiology Division, Inc., St. Paul, MN (US)

(72) Inventors: Ram Kumar Balachandran, Maple Grove, MN (US); Ramji T. Venkatasubramanian, Maple Grove, MN (US); Anthony David Hill, Minneapolis, MN (US); John Hauck, Shoreview, MN (US); Neelakantan Saikrishnan, Plymouth, MN (US); Riki Thao, Little Canada, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 482 days.

(21) Appl. No.: 14/615,996

(22) Filed: Feb. 6, 2015

(65) Prior Publication Data
US 2015/0223729 A1 Aug. 13, 2015

Related U.S. Application Data

(60) Provisional application No. 61/937,155, filed on Feb. 7, 2014.

(51) Int. Cl.
*A61B 5/04* (2006.01)
*A61B 5/107* (2006.01)
(Continued)

(52) U.S. Cl.
CPC .......... *A61B 5/1076* (2013.01); *A61B 5/6853* (2013.01); *A61B 2562/0209* (2013.01); *A61F 2/2496* (2013.01)

(58) Field of Classification Search
CPC .... A61B 5/1076; A61B 5/6853; A61F 2/2496
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 A1 7/2000
DE 10121210 A1 11/2002
(Continued)

OTHER PUBLICATIONS

Andersen, Henning Rud, Transluminal Catheter Implanted Prosthetic Heart Valves, International Journal of Angiology 7:102-106 (1998).
(Continued)

*Primary Examiner* — Robert N Wieland
(74) *Attorney, Agent, or Firm* — Lerner, David, Littenberg, Krumholz & Mentlik, LLP

(57) ABSTRACT

A system for detecting the dimensions and geometry of a native valve annulus for trans-catheter valve implantation includes a compliant balloon and a shaft within the balloon. One or more drive electrodes may be affixed to a surface of the balloon, and one or more sense electrodes may be affixed to the shaft. After insertion of the balloon into the native valve annulus, the drive electrodes may be energized with a predetermined voltage. Using a trained statistical model and the voltages measured at the sense electrodes, initial estimates of the cross-section of the valve annulus may be obtained. The initial estimates may then be provided to an optimization model of the valve annulus to obtain a highly accurate prediction of the cross-section of the valve annulus.

20 Claims, 21 Drawing Sheets

(51) Int. Cl.
*A61B 5/00* (2006.01)
*A61F 2/24* (2006.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,553,611 A | 9/1996 | Budd et al. |
| 5,662,108 A | 9/1997 | Budd et al. |
| 5,843,167 A | 12/1998 | Dwyer et al. |
| 5,855,601 A | 1/1999 | Bessler et al. |
| 5,935,163 A | 8/1999 | Gabbay |
| 5,961,513 A | 10/1999 | Swanson et al. |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,939,309 B1 | 9/2005 | Beatty et al. |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,263,397 B2 | 8/2007 | Hauck et al. |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0120318 A1 | 6/2003 | Hauck |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0221643 A1 | 9/2008 | Olson |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0005674 A1 | 1/2009 | Saadat et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0094328 A1 | 4/2010 | O'Dea et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0228192 A1 | 9/2010 | O'Dea et al. |
| 2010/0228202 A1 | 9/2010 | O'Dea et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2010/0312181 A1 | 12/2010 | O'Dea |

(56) References Cited

U.S. PATENT DOCUMENTS

| | | |
|---|---|---|
| 2011/0029072 A1 | 2/2011 | Gabbay |
| 2011/0054395 A1 | 3/2011 | O'Dea et al. |
| 2012/0035642 A1 | 2/2012 | O'Dea et al. |
| 2012/0065585 A1 | 3/2012 | O'Dea |
| 2012/0277525 A1 | 11/2012 | O'Dea |
| 2013/0123694 A1 | 5/2013 | Subramaniyan et al. |
| 2014/0296706 A1* | 10/2014 | Chronos ............... A61F 2/2496 600/424 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| EP | 2476453 A1 | 7/2012 |
| FR | 2847800 A1 | 6/2004 |
| FR | 2850008 A1 | 7/2004 |
| WO | 9117720 B1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 2006090351 A1 | 8/2006 |
| WO | 07071436 A2 | 6/2007 |
| WO | 08070797 A2 | 6/2008 |
| WO | 2009001325 A1 | 12/2008 |
| WO | 2009001326 A1 | 12/2008 |
| WO | 2009001327 A2 | 12/2008 |
| WO | 2009001328 A2 | 12/2008 |
| WO | 2009081387 A1 | 7/2009 |
| WO | 2009125380 A1 | 10/2009 |
| WO | 10008548 A2 | 1/2010 |
| WO | 10008549 A1 | 1/2010 |
| WO | 10096176 A1 | 8/2010 |
| WO | 10098857 A1 | 9/2010 |
| WO | 2010103501 A1 | 9/2010 |
| WO | 2010103502 A2 | 9/2010 |
| WO | 2011042893 A1 | 4/2011 |
| WO | 2011117852 A1 | 9/2011 |

OTHER PUBLICATIONS

Catheter-implanted prosthetic heart valves, Knudsen, L.L., et al., The International Journal of Artificial Organs, vol. 16, No. 5 1993, pp. 253-262.

Extended European Search Report for Application No. 15154142.2 dated Jun. 8, 2015.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Quaden, René et al., "Percutaneous aortic valve replacement: resection before implantation," 836-840, European J. of Cardio-thoracic Surgery 27 (2005).

Ruiz, Carlos, "Overview of PRE-CE Mark Transcatheter Aortic Valve Technologies", Euro PCR, May 25, 2010.

Transluminal Aortic Valve Placement, Moazami, Nader, et al., ASAIO Journal, 1996; 42:M381-M385.

Transluminal implantation of artificial heart valves, Andersen, H. R., et al., European Heart Journal (1992) 13, 704-708.

U.S. Appl. No. 29/375,243, filed Sep. 20, 2010.

U.S. Appl. No. 29/375,260, filed Sep. 20, 2010.

* cited by examiner

SYSTEM AND METHOD FOR ASSESSING DIMENSIONS AND ECCENTRICITY OF VALVE ANNULUS FOR TRANS-CATHETER VALVE IMPLANTATION

CROSS-REFERENCE TO RELATED APPLICATION

This application claims priority to Provisional Application No. 61/937,155, entitled "System and Method for Assessing Dimensions and Eccentricity of Valve Annulus for Trans-Catheter Valve Implantation," filed on Feb. 7, 2014, the disclosure of which is herein incorporated by reference herein in its entirety.

BACKGROUND OF THE INVENTION

Trans-catheter aortic valve replacement ("TAVR") has been shown to improve the survival rate in high risk patients for whom surgical heart valve replacement is not an option. However, the long-term clinical success of a TAVR or any trans-catheter aortic valve implantation ("TAVI") procedure is dependent on accurate deployment, anchoring and acceptable valve performance, both acutely and chronically. This requires maximum reduction or potential elimination of the risks associated with paravalvular (PV) aortic regurgitation (AR). An additional factor that contributes to the problem of selecting a proper valve size is the eccentricity/elliptical nature of the cross-section of the native valve annulus.

There are a number of ways in which the valve annulus may be sized. Current techniques include imaging techniques such as trans-thoracic echocardiogram (TTE), trans-esophageal echocardiogram (TEE), and angiography. However, these imaging methods are not standardized and may yield different results depending on the view obtained of the annulus with the annulus' elliptic shape contributing to the uncertainty. Although valve-sizing using 3D computed tomographic (CT) imaging has been observed to result in less PV AR, this technique is expensive and requires independent patient preparation/assessment prior to the implantation or valvuloplasty procedure and also poses the risk of exposure to harmful radiation. Thus, there is a clinical need for an alternative option for TAVI sizing that is cost effective.

In addition, alterations to the valve annulus following a balloon valvuloplasty procedure can make it difficult to correctly size the annulus, even with current imaging techniques. For example, it is expected that a valve's annulus dimensions are altered after a balloon valvuloplasty procedure, intended to open up the diseased native valve. However, some imaging techniques, like CT, are performed pre-procedurally and do not provide the altered dimensions of the annulus after this procedure has been performed.

SUMMARY OF INVENTION

The disclosed systems and methods enable a physician to assess dimensions during/post valvuloplasty and thus address the foregoing problems.

In one embodiment, a system is disclosed for determining the dimensions and geometry of a native valve annulus for trans-catheter valve implantation. The system may include a balloon having an interior surface, a shaft located within the balloon and extending longitudinally relative to the interior surface of the balloon, a first pair of drive electrodes affixed to the interior surface of the balloon, the first pair of drive electrodes configured to produce a first electrical field based on a first predetermined current/voltage, a second pair of drive electrodes affixed to the interior surface of the balloon, the second pair of drive electrodes configured to produce a second electrical field based on a second predetermined current/voltage, a first pair of sense electrodes affixed to a surface of the shaft, the first pair of sense electrodes configured to detect the first and second electrical field, and a second pair of sense electrodes affixed to the surface of the shaft, the second pair of sense electrodes configured to detect the first and second electrical field. According to one aspect of the system, the balloon may be made of an insulative material such that the first electrical field and the second electrical field are confined to an area inside the balloon.

In a further aspect of the system, the first pair of sense electrodes is affixed to a midpoint of the shaft.

In yet another aspect of the system, the electrodes that comprise the two drive pairs are affixed approximately 180° apart on the interior surface. The first and the second drive electrode pair are also affixed approximately 90° degrees apart on the interior surface. Additionally the electrodes that comprise the two sense pairs are affixed approximately 180° apart on the shaft. The first and the second sense electrode pairs are also affixed approximately 90° apart on the shaft.

In yet a further aspect of the system, the system includes a third pair of drive electrodes affixed to the surface of the shaft, at least one electrode of the third pair of drive electrodes being positioned a distance in a first longitudinal direction from the first sense electrode pair, and the other electrode of the third pair of electrodes being positioned the distance in a second longitudinal direction opposite the first longitudinal direction from the first sense electrode, and a third sense electrode pair affixed to the surface of the shaft, the third sense electrode pair being positioned a distance apart near the mid-point of the shaft. The third sense electrode pair is configured to detect the third electrical field generated by the third pair of drive electrodes.

A method for determining the dimensions and geometry of a native valve annulus for trans-catheter valve implantation is also disclosed. In one aspect, the method includes loading a balloon catheter in a delivery system, the balloon catheter having a balloon with a first surface and a second surface, a shaft located within the balloon and extending longitudinally relative to the interior surface of the balloon, a first pair of electrodes affixed to the interior surface of the balloon, a second pair of electrodes affixed to the interior surface of the balloon, a first sense electrode pair affixed to a surface of the shaft, and second sense electrode pair affixed to the surface of the shaft. The method may also include delivering the balloon catheter to a native valve annulus, deploying the balloon catheter within the valve annulus so that the balloon conforms to a surface of the valve annulus, applying a first current to the first pair of electrodes to produce a first electrical field, applying a second current to the second pair of electrodes to produce a second electrical field, detecting the first and second electrical field with the first and second sense electrode pairs, and determining one or more dimensions of the valve annulus based at least on the detected first electrical field and the detected second electrical field. In another aspect of the method, the balloon may be made of an electrically insulative material such that the first electrical field and the second electrical field are confined to an area inside the balloon.

In a further aspect of the method, the first sense electrode pair is affixed to a midpoint of the shaft.

In yet another aspect of the method, the electrodes that comprise the two drive pairs are affixed approximately 180° apart on the interior surface. The first and the second drive electrode pair are also affixed approximately 90° degrees apart on the interior surface. Additionally the electrodes that comprise the two sense pairs are affixed approximately 180° apart on the shaft. The first and the second sense electrode pairs are also affixed approximately 90° apart on the shaft.

In yet a further aspect of the method, the balloon catheter may further include a third pair of drive electrodes affixed to the surface of the shaft, at least one electrode of the third pair of drive electrodes being positioned a distance in a first longitudinal direction from the first sense electrode pair, and the other electrode of the third pair of electrodes being positioned the distance in a second longitudinal direction opposite the first longitudinal direction from the first sense electrode, and a third sense electrode pair affixed to the surface of the shaft, the third sense electrode pair being positioned a distance apart near the mid-point of the shaft. The method may also include applying a third current to the third pair of electrodes to produce a third electrical field, detecting the third electrical field with the third sense electrode pair, and further determining the one or more dimensions of the native valve annulus based at least on the detected third electrical field.

Another system is also disclosed for determining the dimensions and geometry of a native valve annulus for trans-catheter valve implantation. In one aspect, the system may include a non-transitory, computer-readable medium comprising computer-executable instructions, and one or more processors in communication with the non-transitory, computer-readable medium.

When the computer-executable instructions are executed, one or more processors may be configured to receive first voltage values from a first sense electrode pair affixed to a shaft of a balloon catheter and configured to detect first and second electrical fields produced by first and second pair of drive electrodes, receive second voltage values from a second sense electrode pair affixed to the shaft of the balloon catheter and configured to detect first and second electrical fields produced by first and second pair of drive electrodes, determine a major axis length of a native valve annulus based on the detected first and second voltage values, determine a minor axis length of the native valve annulus based on the detected first and second voltage values, and determine an eccentricity of the native valve annulus based on the determined major axis length and the determined minor axis length.

In another aspect of the system, the one or more processors are further configured to determine the major axis length based on an estimate of the major axis length.

In a further aspect of the system, the one or more processors are further configured to determine an estimated major axis length of the native valve annulus by providing the received voltages from the first and second sense electrode pairs to a statistical model of the native valve annulus, and determine the actual major axis length of the native valve annulus by providing the estimated major axis length to an optimization model of the native valve annulus.

In yet another aspect of the system, the one or more processors are further configured to determine the minor axis length based on an estimate of the minor axis length.

In yet a further aspect of the system, the one or more processors are further configured to determine at least one offset value associated with the balloon catheter based on the detected first and second electrical fields, wherein the at least one offset value identifies an amount of offset of an axis of the balloon catheter relative to an axis of the native valve annulus.

Another method for determining the dimensions and geometry of a native valve annulus for trans-catheter valve implantation may include receiving, with one or more processors, voltage values from first and second sense electrode pairs affixed to a shaft of a balloon catheter and configured to detect a first and second electrical field produced by a first and second pair of drive electrodes. The method may also include determining with the one or more processors, a major axis length of the native valve annulus based on the received voltage values from the first and second sense electrode pairs and determining, with the one or more processors, a minor axis length of the native valve annulus based on the received voltage values from the first and second sense electrode pairs. The method may further include determining an eccentricity of the native valve annulus based on the determined major axis length and the determined minor axis length.

In another aspect of the method, the method may include determining the major axis length based on an estimate of the major axis length.

In a further aspect of the method, the method may include determining an estimated major axis length of the native valve annulus by providing the first and second voltage values to a statistical model of the native valve annulus, wherein the step of determining the major axis length of the native valve annulus includes providing the estimated major axis length to an optimization model of the native valve annulus.

In yet another aspect of the method, the method may include determining the minor axis length based on an estimate of the minor axis length.

In yet a further aspect of the method, the method may include determining at least one offset value associated with the balloon catheter based on the received first and second voltage values, wherein the at least one offset value identifies an amount of offset of an axis of the balloon catheter relative to an axis of the native valve annulus.

Another aspect of the disclosure describes a method for determining the dimensions and geometry of a native valve annulus for trans-catheter valve implantation that includes loading a balloon catheter in a delivery system. The balloon catheter may include a balloon extending in a longitudinal direction, a shaft extending in the longitudinal direction within the balloon, a plurality of splines connected to the shaft, a first pair of electrodes on a first pair of the splines, and a second pair of electrodes on a second pair of the splines. Accordingly, the method may include delivering the balloon catheter to the native valve annulus, deploying the balloon catheter at a first longitudinal position within the native valve annulus so that the balloon conforms to a surface of the native valve annulus at the first longitudinal position, deploying the plurality of splines so that the splines move radially outward from the shaft, applying a first current to the first pair of electrodes to produce a first electrical field, measuring, using the second pair of electrodes, values associated with the first electrical field, applying a second current to the second pair of electrodes to produce a second electrical field; measuring, using the first pair of electrodes, values associated with the second electrical field, and determining one or more dimensions of the native valve annulus based at least on the values associated with the first electrical field and the second electrical field.

In some aspects, the balloon catheter may include a central ring electrode located on the shaft that may be used to measure values associated with the first electrical field and the second electrical field.

In another aspect, the balloon catheter may include a third pair of electrodes on a third pair of the plurality of splines. Accordingly, the method may include applying a third current to the third pair of electrodes to produce a third electrical field and measuring values associated with the third electrical field using the first pair of electrodes and the second pair of electrodes. Additionally, the balloon catheter may include a fourth pair of electrodes on a fourth pair of the plurality of splines. According to this aspect, the method may include applying a fourth current to the fourth pair of electrodes to produce a fourth electrical field and measuring values associated with the fourth electrical field using the first pair of electrodes, the second pair of electrodes, and the third pair of electrodes.

In yet another aspect, the method may include re-deploying the balloon catheter at a second longitudinal position within the native valve annulus so that the balloon conforms to the surface of the native valve annulus at the second longitudinal position, applying a third current to the first pair of electrodes to produce a third electrical field, measuring, using the second pair of electrodes, values associated with the third electrical field, applying a fourth current to the second pair of electrodes to produce a fourth electrical field, measuring, using the first pair of electrodes, values associated with the fourth electrical field, and determining one or more secondary dimensions of the native valve annulus based at least on the values associated with the third electrical field and the fourth electrical field. In this regard, the method may include obtaining three-dimensional information about the native valve annulus by combining the one or more dimensions of the native valve annulus and the one or more secondary dimensions of the native valve annulus.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the words "substantially," "approximately," "generally," and "about" are intended to mean that slight variations from absolute are included within the scope of the structure or process recited.

This disclosure provides for a system and method for determining various dimensions of a native valve annulus. In particular, the native valve annulus may be a valve annulus in which a trans-catheter aortic valve is to be implanted. The native valve annulus may also be that in which another type of trans-catheter cardiac valve is to be implanted, such as a mitral valve, a tricuspid valve, or a pulmonary valve. Alternatively, native valve may refer to a previously implanted prosthetic valve in a patient which is diseased that requires further intervention using a new trans-catheter valve implantation procedure ("valve-in-valve" implantation). The disclosed system and method use electrical fields generated by electrodes to determine the major and/or minor diameters of the native valve annulus. Alternatively, the disclosed system and method may use magnetic fields to determine the major and/or minor diameters of the native valve annulus. The disclosed systems and methods described herein take advantage of the balloon valvuloplasty procedure that usually precedes valve implantation.

During balloon valvuloplasty, a balloon catheter is inflated with saline that results in the flattening of the native valve leaflets, which are typically diseased and/or calcified. A non-compliant balloon is typically used for this purpose.

Figure 1:
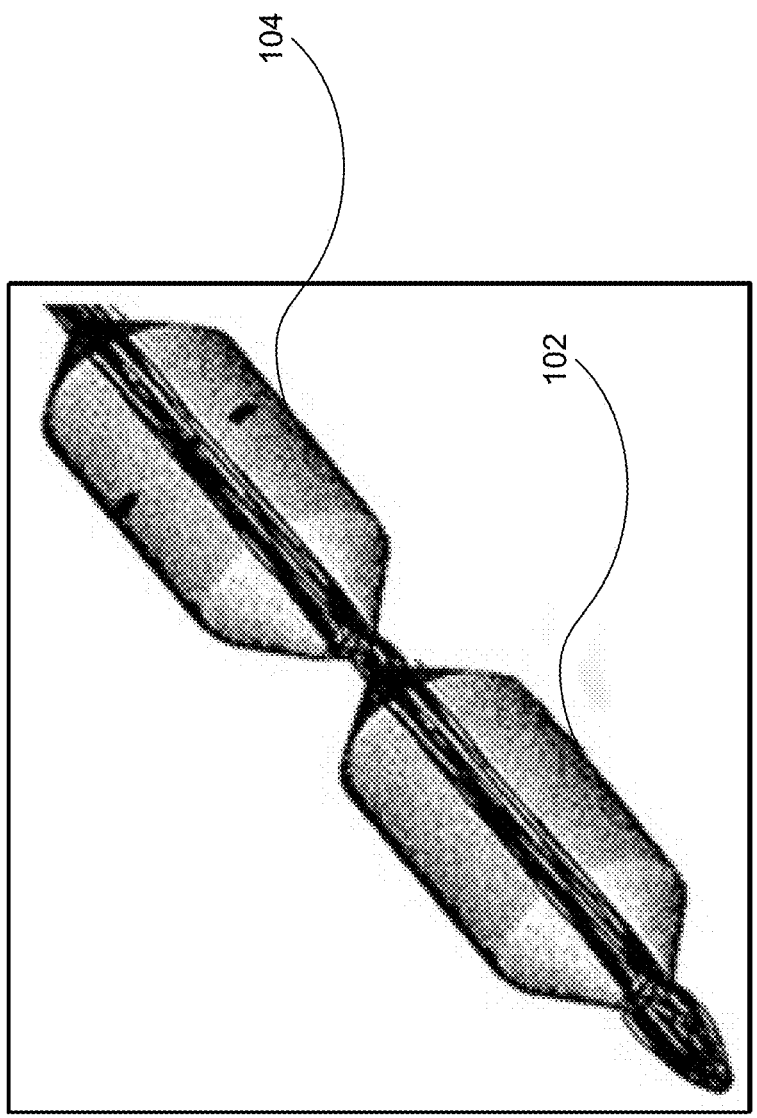
FIG. 1 is a perspective view of an exemplary balloon catheter according to aspects of the disclosure.

In one embodiment, the disclosed system and method add another balloon, typically a compliant balloon, either proximal or distal to the valvuloplasty balloon. FIG. 1 illustrates one example of a non-compliant balloon 102 having the compliant balloon 104 placed adjacent to it.

According to one embodiment, the physician may inflate and deflate the non-compliant balloon 102 to perform a balloon valvuloplasty procedure, then either advance or retract the catheter and inflate the compliant (i.e., sizing) balloon 104 to measure the dimensions of the native valve annulus.

Furthermore, the compliant balloon 104 may share a fluid lumen with the non-compliant balloon 102. Alternatively, the fluid lumens may be separate. When inflated, the compliant balloon 104 may conform to the native valve annulus such that the walls of the balloon 104 contact substantially the entire circumference of the valve annulus or as much of the circumference of the valve annulus as is physically possible (e.g., there may be slight gaps between the balloon wall and the circumference of the valve annulus).

In an alternative approach, the compliant balloon 104 may be a stand-alone device having its own shaft (not shown). In cases in which valvuloplasty is not performed prior to valve implantation, this stand-alone device may be used for sizing the native valve annulus. Alternatively, the stand-alone device may be used in conjunction with valvuloplasty by exchanging the valvuloplasty catheter with the sizing catheter over the same wire.

Figure 2:
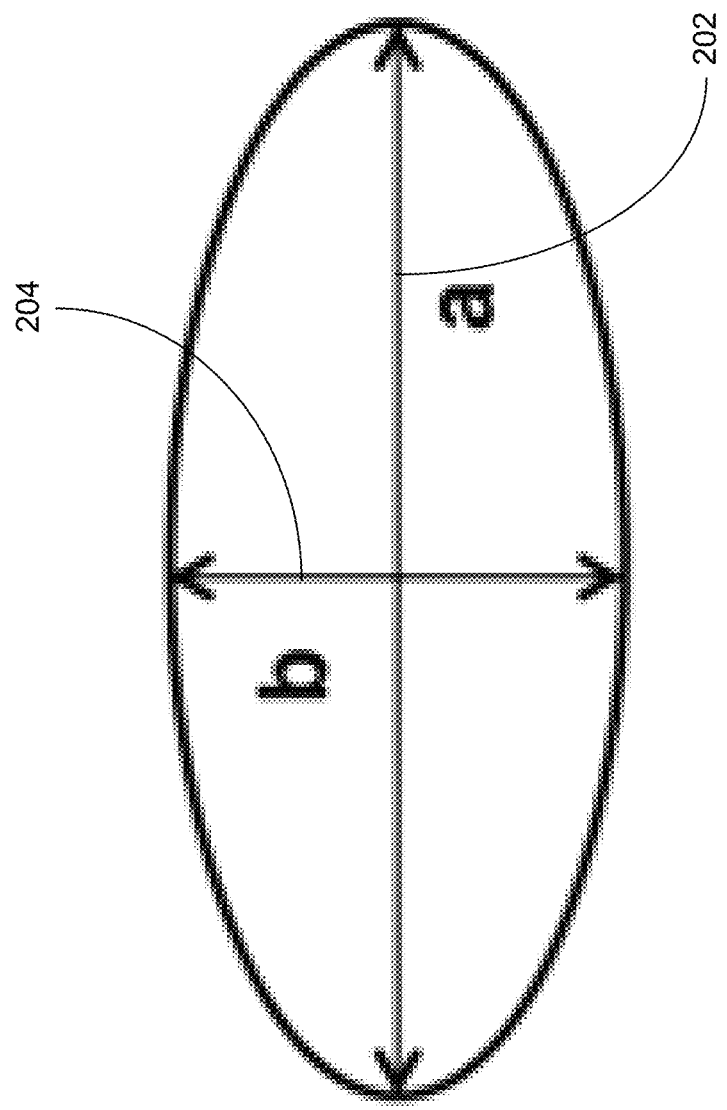
FIG. 2 is a diagrammatic view illustrating the elliptical dimensions of a native valve annulus that may be determined according to aspects of the disclosure.

FIG. 2 illustrates an example of the dimensions of the native valve annulus that may be measured by the disclosed system and method. In one embodiment, the dimensions may include the lengths of a major axis 202 and a minor axis 204. The dimensions of the major axis 202 and the minor axis 204 may be approximate or estimated, and within a degree of confidence. From these dimensions, other aspects of the native valve annulus may also be determined, such as its eccentricity. As discussed below, these dimensions may be determined through the assistance of one or more methods, based on statistical and/or optimization techniques.

In one embodiment, sizing of the native valve annulus with the sizing balloon may be performed by establishing an electric field inside the balloon 104 with a drive current of known or measured amplitude and measuring resulting voltages. By dividing the measured voltages by the drive current used, respective resistances may be calculated. The more general term "impedance" may be used instead of resistance. However, in one preferred embodiment, the relevant potential distribution resulting from the drive current may be in phase with the voltage waveform. As such, the capacitive components will be minimal. In other words, the real or resistive component is sought. The resistances will be a function of the electrode distribution, the balloon geometry, and the conductivity of the solution used. To normalize for conductivity, a solution of known conductivity may be used. Alternatively, the conductivity may be measured in real time as part of the measurement system. In one implementation, it may be preferable to have the available resistance values, after scaling with the solution conductivity measurement, be a function of only the geometric parameters that are sought.

Figure 3:
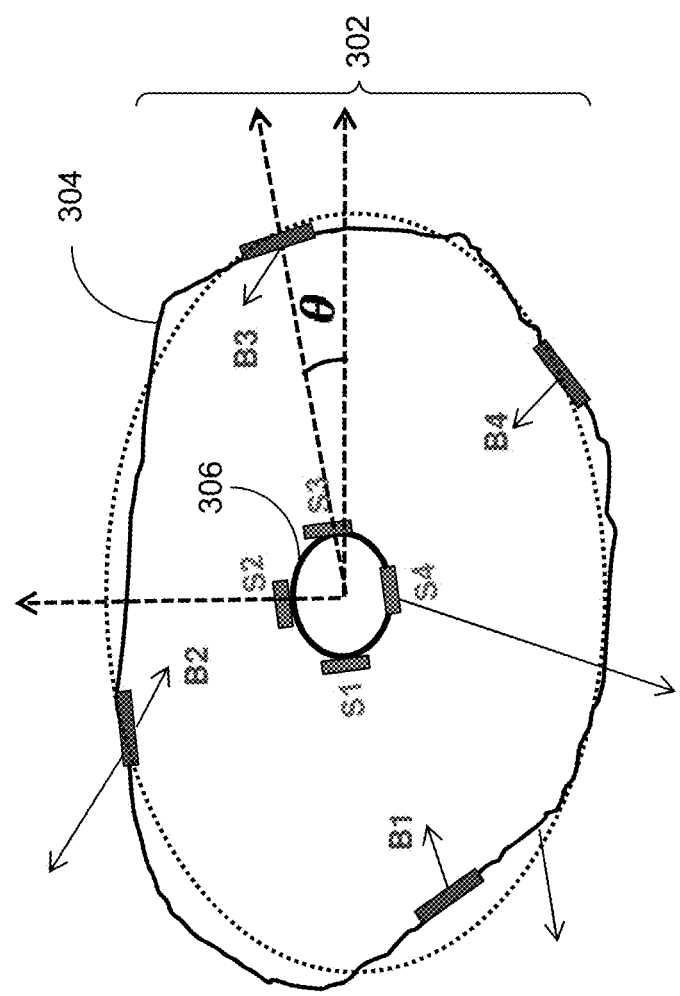
FIG. 3 is a schematic transverse cross-sectional view of a balloon catheter with electrodes according to aspects of the disclosure.

FIG. 3 illustrates a schematic transverse cross-sectional view of a balloon catheter 302 with drive electrodes B1-B4 for generating the electrical field and sense electrodes S1-S4 for measuring the resulting voltages and/or impedance values. The balloon catheter 302 may include a balloon 304 and a shaft 306. The balloon catheter 302 may be filled with a homogenous medium, such as isotonic saline, whose electrical conductivity may be determined through prior calibration. Alternatively, a saline solution of a priori known conductivity may be used. Since saline conductivity is a function of temperature, a thermistor may be included inside the balloon 304 to measure temperature and facilitate correction of the conductivity through the use of computer software or the like.

Electrodes B1-B4 and S1-S4 may be placed on one or more surfaces of the balloon 304 and/or the shaft 306. For example, four drive (i.e., 2 source and 2 sink) electrodes (B1, B2, B3, B4) may be placed at circumferentially spaced positions on the inside surface of the balloon 304, and four sense electrodes (S1, S2, S3, S4) may be placed at circumferentially spaced positions on the outside surface of the shaft 306. In one embodiment, the drive electrodes B1-B4 may be placed such that they are equally spaced on the inside surface of the balloon 304, and the sense electrodes S1-S4 may be placed such that they are equally spaced on the circumference of the shaft 306 that lies inside the balloon 304.

The balloon electrodes B1-B4 may be placed either by coating the outside surface of the balloon 304 with conductive ink or by affixing flexible electrode material to the outside surface of the balloon 304 and then flipping the balloon 304 inside out. Other techniques for depositing conductive material on the electrically insulative balloon substrate may also be used. These techniques may include, but are not limited to, low temperature print manufacturing (with or without sintering), electroplating, electroless plating, sputter deposition, heat, mechanical deformation, cathodic arc deposition, evaporative deposition, pulsed laser deposition or combinations thereof. Split-ring electrodes may be placed on the shaft 306 using manual methods or any of the above-mentioned metal deposition techniques and used as sense electrodes S1-S4.

The electrodes may be placed at predetermined distances and/or predetermined angles from one another. For example, the drive electrodes B1-B4 and/or the sense electrodes S1-S4 may be placed 90° apart as shown in FIG. 3. In one embodiment, drive electrodes B1-B4 may be substantially radially aligned with their corresponding sense electrodes S1-S4. In another embodiment, there may be a fixed degree of angular offset between the drive electrodes B1-B4 and one or more of the sense electrodes S1-S4. Further still, the positions of the drive electrodes B1-B4 and the sense electrodes S1-S4 may be swapped. That is, the drive electrodes B1-B4 may be positioned on the shaft 306 and the sense electrodes S1-S4 may be positioned on the inside surface of the balloon 304.

When a small current is driven between pairs of drive electrodes B1-B4, each of the sense electrodes S1-S4 may detect a current and/or a voltage. In one embodiment, a current of 1 mA may be applied to one or more pairs of drive electrodes B1-B4. As the electrical field generated by the drive electrodes B1-B4 may be confined to the interior of the balloon 304, and as the conductivity of the medium through which the electrical field passes (e.g., saline) may be known, the resulting measured voltages and/or impedances from the sense electrodes S1-S4 provide the native annulus dimensional information.

In measuring the electrical field generated by the drive electrodes B1-B4, one pair of drive electrodes along a first cross-sectional axis of the balloon 304 (e.g., B1 and B3) may be energized and the sense electrodes (e.g., S1-S4) may be used to measure/sense the voltage from the resulting electrical field. The measurement may be performed in a variety of ways, such as by using a differential electronic measurement or by choosing a dedicated electrode as a reference electrode for all measurements.

The pair of electrodes being energized may then be switched to the pair of electrodes along the second cross-sectional axis of the balloon 304 (e.g., B2 and B4), and similar measurements at the sense electrodes (e.g., S1-S4) may be performed. In other words, a first pair of drive electrodes along a first cross-sectional axis of the balloon 304 may be energized and then a second pair of drive electrodes along a second cross-sectional axis of the balloon 304 may be energized. While a single pair of drive electrodes may be energized at any one time (e.g., B1 and B3 or B2 and B4), it is also possible to energize the drive electrodes in other pairwise combinations (e.g., (B1, B2), (B1, B4), (B2, B3), etc.).

Voltage values measured by the sense electrodes S1-S4 may vary, but for a 1 mA drive current, the voltage values are expected to be in the 0-25 mV range for a saline conductivity of 1 S/m with an ellipsoidal balloon having dimensions of 20-30 mm on the major axis and 20-30 mm on the minor axis. As the conductivity of the saline in the balloon catheter may be evaluated a priori, the measured voltages and the calculated impedance values may be a function of the balloon geometry.

Information about the geometry of the cross-section of the native annulus may then be calculated from the voltages measured by the sense electrodes S1-S4. In particular, and as discussed above, the measured dimensions may include the length of the major axis (a) of the native annulus, the length of the minor axis (b) of the native annulus, and the rotational orientation of the ellipse (θ) with respect to the balloon catheter 302. Since a native valve annulus is not perfectly circular or elliptical, the measured dimensions of the native valve annulus may be a best-fit estimate. As discussed further below, an inverse solution method based on an optimization scheme may be used to evaluate the geometrical parameters.

Figure 4:
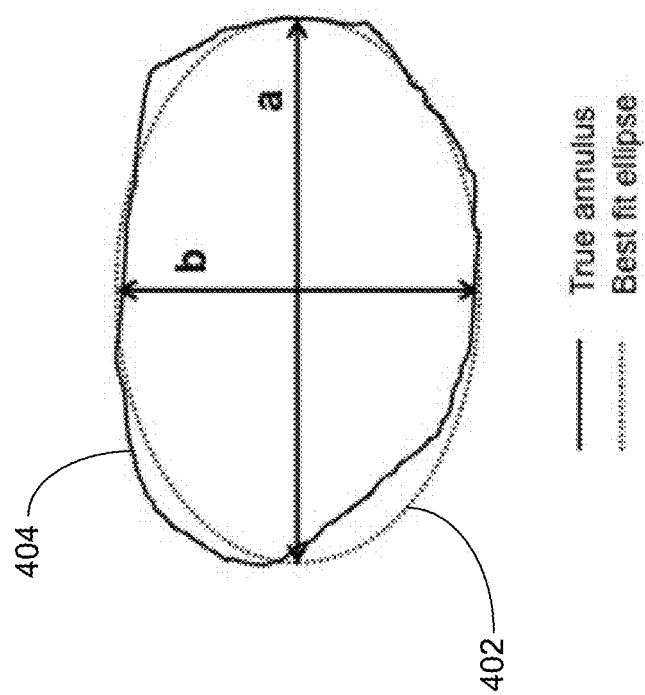
FIG. 4 is a diagrammatic view illustrating an example of estimating the dimensions of a native valve annulus according to aspects of the disclosure.

FIG. 4 illustrates an example of estimating the dimensions of a native valve annulus according to aspects of the disclosure. The example illustrates that the voltages detected by one or more of the sense electrodes S1-S4 may provide a best-fit estimate 402 of the actual dimensions 404 of the native valve annulus. Additional electrodes may further refine this best fit estimate and/or provide additional dimensional information for the native valve annulus.

Figure 5:
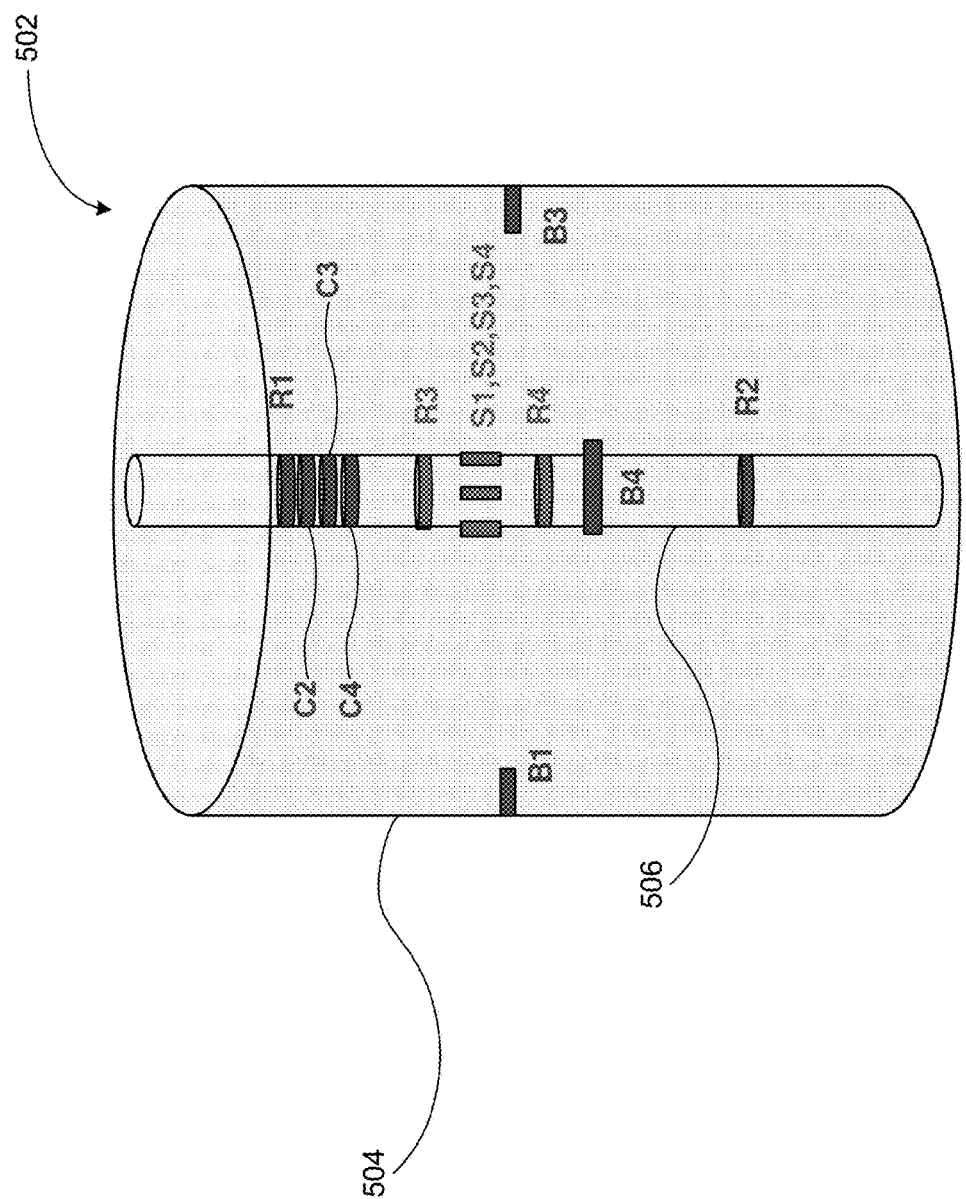
FIG. 5 is a schematic perspective view of a balloon catheter with additional electrodes according to aspects of the disclosure.

FIG. 5 is a schematic perspective view of a balloon catheter 502 with additional electrodes according to aspects of the disclosure. Balloon catheter 502 may be similar to balloon catheter 302, and may include a balloon 504, a shaft 506, drive electrodes B1-B4, and sense electrodes S1-S4 positioned as in balloon catheter 302. In addition to the sense electrodes S1-S4 and drive electrodes B1-B4, balloon catheter 502 may also include circumferential electrodes for obtaining cross-sectional area information of the native valve annulus. In one embodiment, the circumferential electrodes may include drive electrodes R1, R2 and sense electrodes R3, R4. The drive electrodes R1, R2 may be in the form of annular rings around the outside surface of the shaft 506 at predetermined distances from one or more of the sense electrodes S1-S4. The distance between drive electrode R1 and sense electrodes S1-S4 may be approximately equal to the distance between drive electrode R2 and sense electrodes S1-S4. For example, drive electrode R1 may be placed 20 mm to one side of sense electrodes S1-S4 and drive electrode R2 may be placed 20 mm to the opposite side of sense electrodes S1-S4.

In addition, a four-terminal measurement of the electrical impedance of the homogenous medium may be performed using at least two pairs of closely spaced electrodes. For example, as shown in FIG. 5, a pair of current-carrying electrodes (R1 and C4) and a pair of voltage-sensing electrodes (C2 and C3) are shown. A current may be emitted from electrode R1 and returned through electrode C4. The voltage due to the electric field thus generated is measured by the sense electrodes C2 and C4. The measurement can be used to determine the instant electrical conductivity of the homogenous medium.

In performing this type of measurement, the electrode spacing should be very close relative to the cross-sectional dimension of the balloon. This is to provide a measurement that is insensitive to the balloon geometry. For example, if there is a 10 mm space from the shaft 506 in the center of the balloon 504 to the balloon boundary, an electrode spacing between R1 and C4 of 2 mm, with C2 and C3 equally spaced between them, will provide a configuration that will be insensitive to the balloon geometry, but the differential resistance measured between electrode R1 and electrode C4 will scale with solution conductivity.

Figure 6:
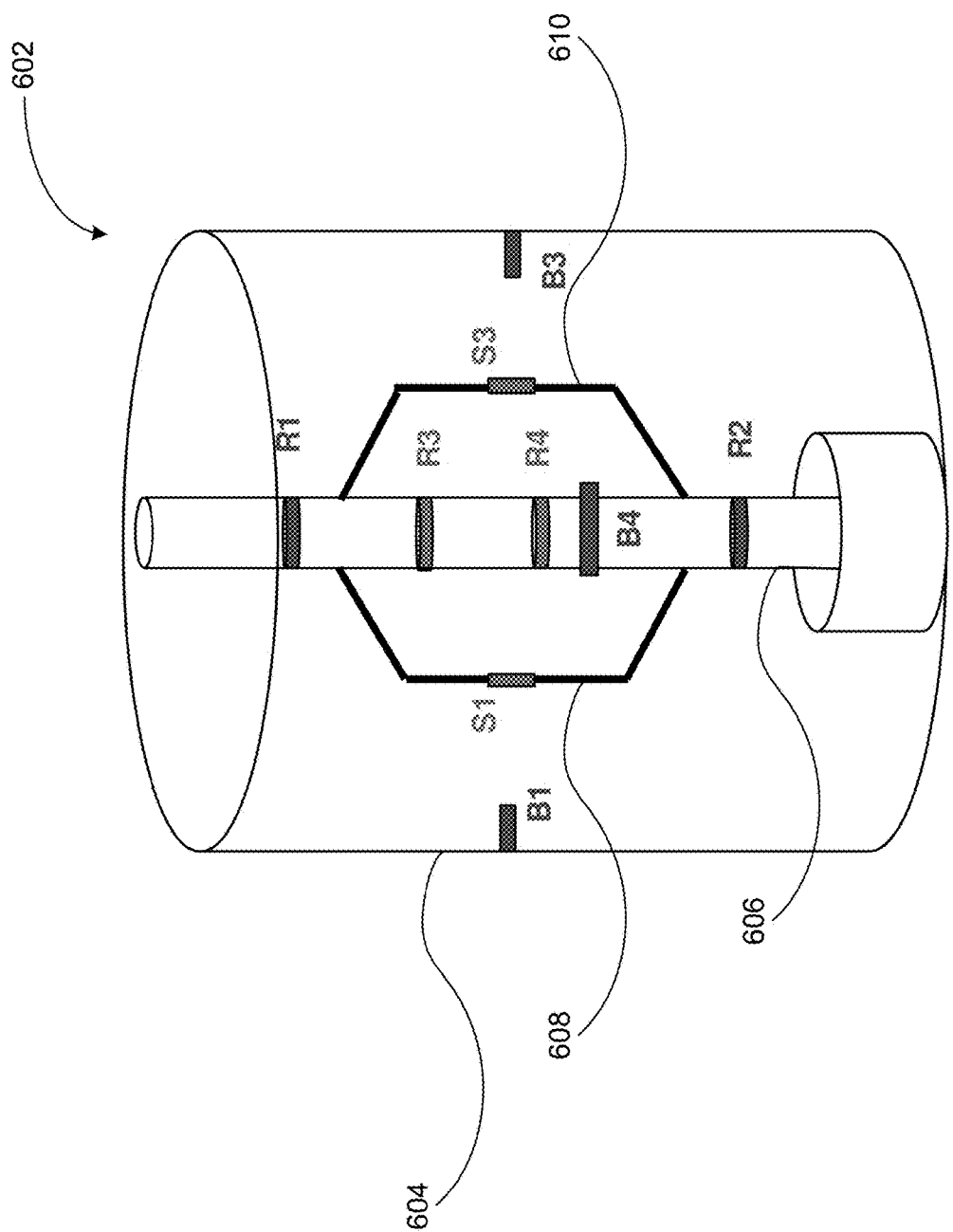
FIG. 6 is a schematic perspective view of another balloon catheter in which the sensing electrodes are placed on splines extending from the shaft of the balloon catheter according to aspects of the disclosure.
Figure 7:
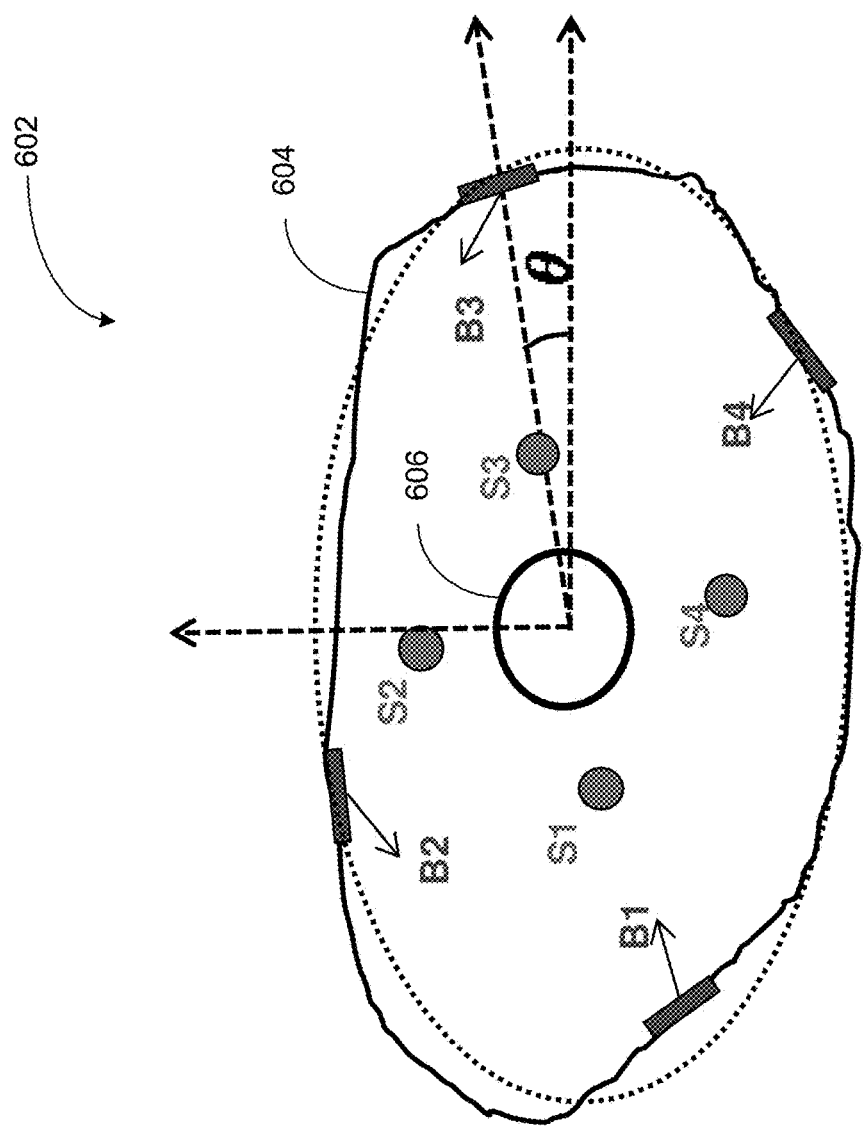
FIG. 7 is a schematic transverse cross-sectional view of the balloon catheter of FIG. 6.

FIGS. 6-7 illustrate a sensing balloon catheter 602 in which electrodes have been mounted on splines extending from, and substantially parallel to, the shaft of the balloon catheter 602. In particular, FIG. 6 shows a balloon catheter 602 having a balloon 604, a shaft 606, and electrodes B1-B4 and R1-R4 mounted at substantially the same positions as in balloon catheter 502. However, in balloon catheter 602, the sensing electrodes S1-S4 are placed on splines extending from the shaft 606 of balloon catheter 602 (only splines 608 and 610 being visible in the figure). FIG. 7 is a transverse cross-sectional view of balloon catheter 602 with sensing electrodes S1-S4 affixed to the splines extending from the shaft 606 of the balloon catheter. Having sensing electrodes S1-S4 placed on corresponding splines extending from the shaft 606 may increase the overall sensitivity of the voltage detection and, thus, provide a more accurate prediction of the dimensions of the valve annulus cross-section. For example, the increase in sensitivity may be due to the decrease in distance between the drive and the sense electrodes and/or to the increase in separation between the sense electrodes.

Figure 8:
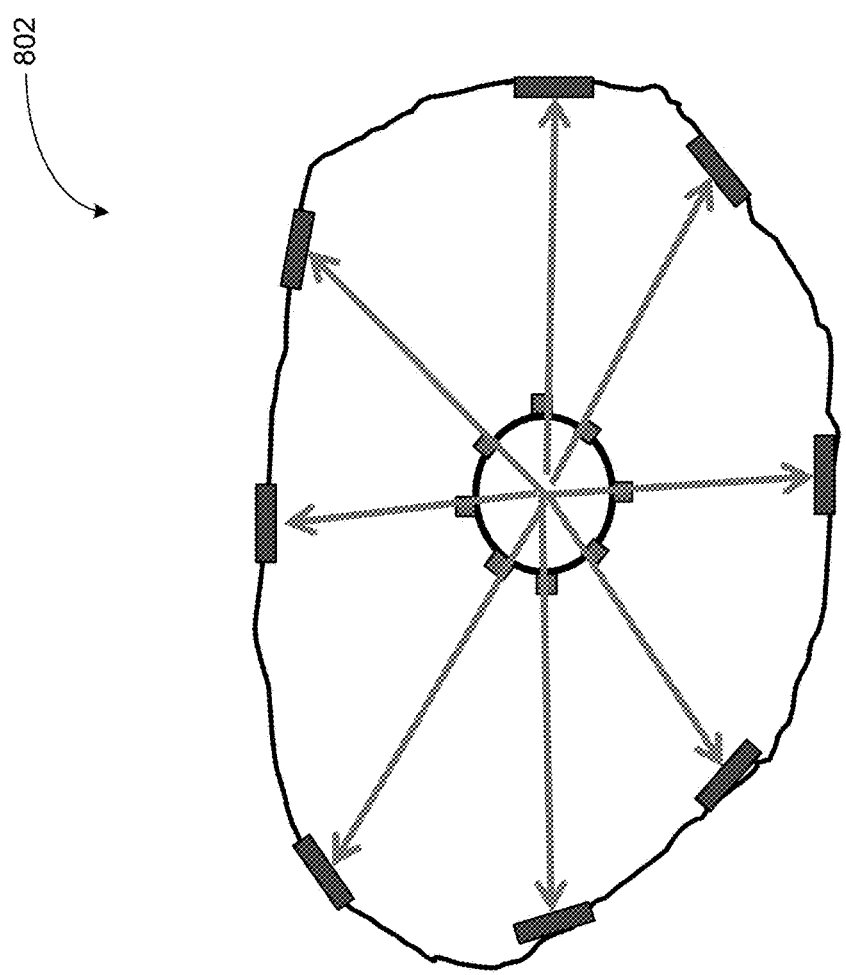
FIG. 8 is a schematic transverse cross-sectional view of a balloon catheter with additional drive electrodes and sensing electrodes according to aspects of the disclosure.

FIG. 8 illustrates an example of a balloon catheter 802 with additional drive electrodes and sensing electrodes according to aspects of the disclosure. The additional drive and sensing electrodes may help determine corresponding spoke radius and diameter dimensions. These additional electrodes may increase the accuracy of the predicted dimensions and/or increase the ability to predict additional geometry details (e.g., the spoke radii) for the irregular geometry of the valve annulus. In other words, the additional drive electrodes and sensing electrodes increase the number of cross-sectional axes that may be measured for a given native valve annulus.

Figure 9A:
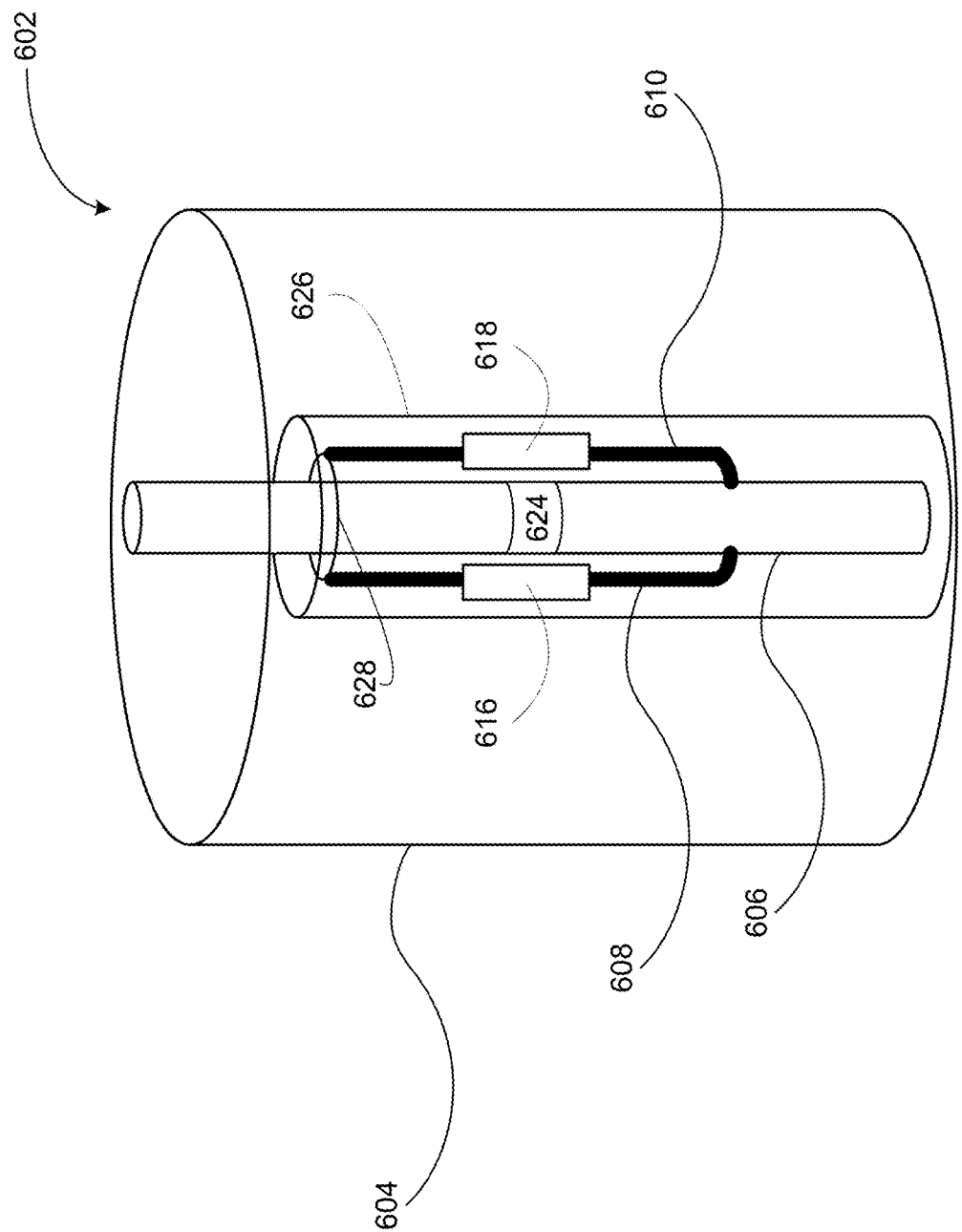
FIGS. 9A and 9B are schematic perspective views of an alternative embodiment of a balloon catheter in which electrodes are placed on splines extending from the shaft of the balloon catheter according to aspects of the disclosure.
Figure 9B:
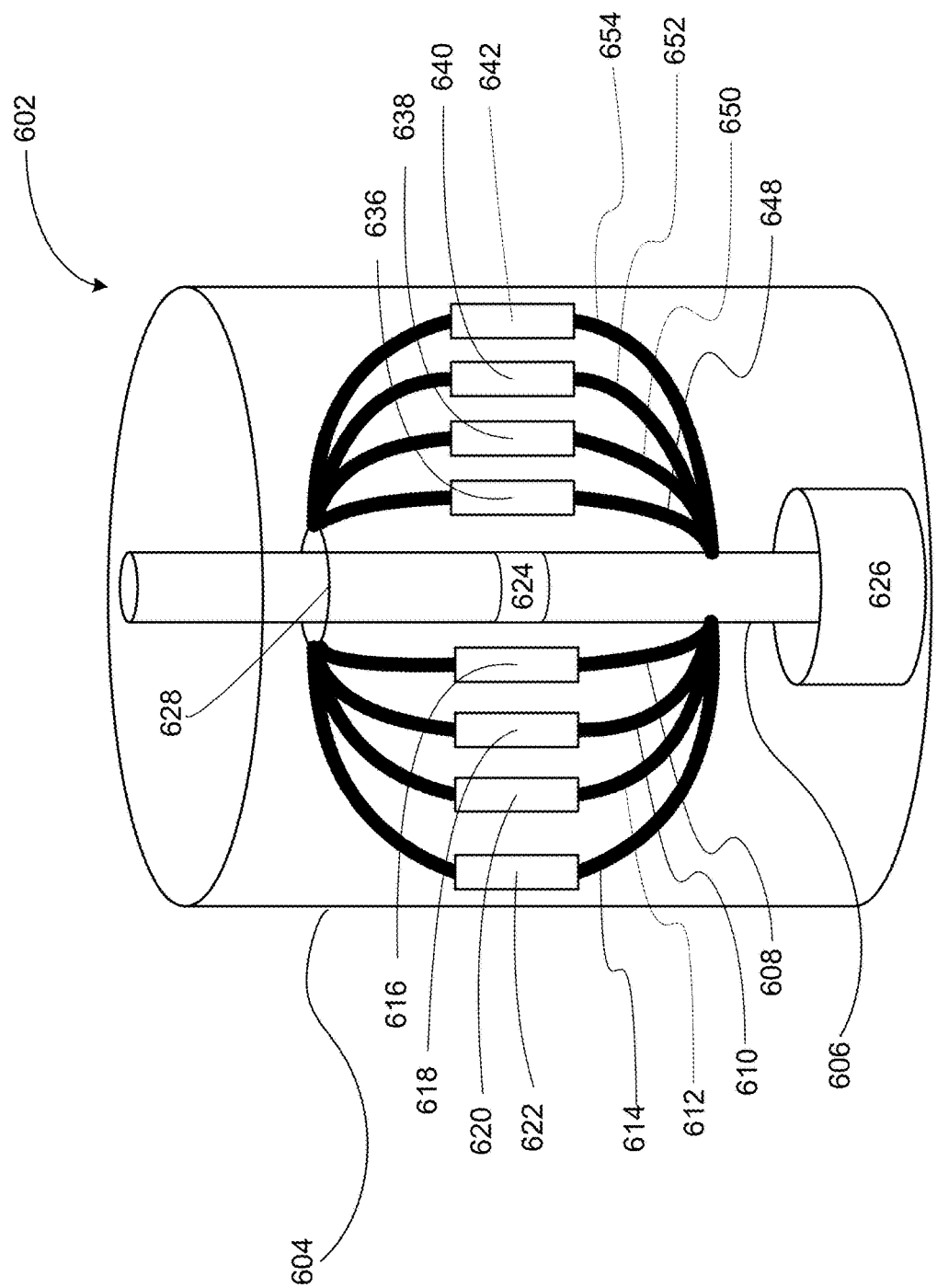

FIGS. 9A and 9B illustrate an alternative embodiment of sensing balloon catheter 602. Sensing balloon catheter 602 includes a balloon 604, a shaft 606, a first spline 608, a second spline 610, a third spline 612, a fourth spline 614, a fifth spline 648, a sixth spline 650, a seventh spline 652, an eighth spline 654, a first electrode 616, a second electrode

618, a third electrode 620, a fourth electrode 622, a fifth electrode 636, a sixth electrode 638, a seventh electrode 640, an eighth electrode 642, a central ring electrode 624, a spline sheath 626, and a sliding ring 628. FIG. 9A shows sensing balloon catheter 602 prior to spline sheath 626 being retracted. While FIG. 9B illustrates 8 splines with an electrode on each spline, one of ordinary skill in the art would recognize that 8 or more splines with an electrode an each spline may be used.

Balloon 604 may be a compliant or non-compliant balloon made from a suitable material, such as an electrically insulative material. As discussed above, balloon 604 may be inflated using a pressurized homogenous medium (e.g., saline) via a fluid lumen such that the balloon would conform to the annulus of the native valve without altering the geometry of the valve annulus. Balloon 604 may be bonded at its distal end to shaft 606 ("inner") and at its proximal end to an outer catheter shaft ("outer") (not shown). According to some examples, shaft 606 may have a lumen for a guide wire.

The central ring electrode 624 may be mounted on shaft 606 to serve as a reference electrode for measurement (e.g., voltage or impedance) of an electrical field generated by the electrodes. Preferably, central ring electrode 624 may be mounted along the equator of shaft 606 (i.e., at the center of the portion of shaft 606 within the balloon). According to some examples, the central ring electrode may be located in the same plane as electrodes 616, 618, 620, 622, 636, 638, 640, and 642. In some embodiments, the central ring electrode 624 may excluded.

The first spline 608, the second spline 610, the third spline 612, the fourth spline 614, the fifth spline 648, the sixth spline 650, the seventh spline 652, and the eight spline 654 may be attached to shaft 606 at their proximal ends. At their distal ends, the splines may come together and connect to sliding ring 628 that can freely slide over shaft 606. Sliding ring 628 enables easy deployment and resheathing of splines 608, 610, 612, 614, 648, 650, 652, and 654 without causing residual stresses.

While eight splines are shown in FIGS. 9A and 9B, sensing balloon catheter 602 may have any number of equally spaced splines. In preferred embodiments, sensing balloon catheter 602 may include 8 or more equally-spaced splines that can expand radially outward such that the electrodes located on the splines may contact the inner wall of the inflated balloon when spline sheath 626 is retracted as shown in FIG. 9B. For example, the splines may expand outward to a diameter that is larger than the largest aortic valve annulus diameter (typically around 30 mm in humans) when fully deployed.

In some embodiments, splines 608, 610, 612, 614, 648, 650, 652, and 654 may be struts formed from a shape-memory material, such as Nitinol, and heat set in the expanded condition so that the splines self-expand to the expanded condition upon the retraction of spline sheath 626. The diameter of the splines may be between about 1 FR and about 3 FR. Preferably, the diameter of the splines may be about 2 FR.

Each spline may have an electrode mounted thereon. As shown in FIGS. 9A and 9B, the first electrode 616 may be mounted on the first spline 608, the second electrode 618 may be mounted on the second spline 610, the third electrode 620 may be mounted on the third spline 612, the fourth electrode 622 may be mounted on the fourth spline 614, the fifth electrode 636 may be mounted on the fifth spline 648, the sixth electrode 638 may be mounted on the sixth spline 650, the seventh electrode 640 may be mounted on the seventh spline 652, and the eighth electrode 642 may be mounted on the eighth spline 654. As discussed above, 8 or more equally-spaced splines may be used in balloon catheter 602.

The electrodes may be any electrode suitable for medical purposes. In some embodiments, electrodes 616, 618, 620, 622, 636, 638, 640, and 642 may be ring electrodes mounted along the waist of each spline. In preferred embodiments, the electrodes may be formed of platinum-iridium, platinum, gold, silver, or stainless steel. The electrodes may be between about 0.5 mm and about 4.5 mm long. In preferred embodiments, the electrodes may be about 1 mm long.

Figure 10:
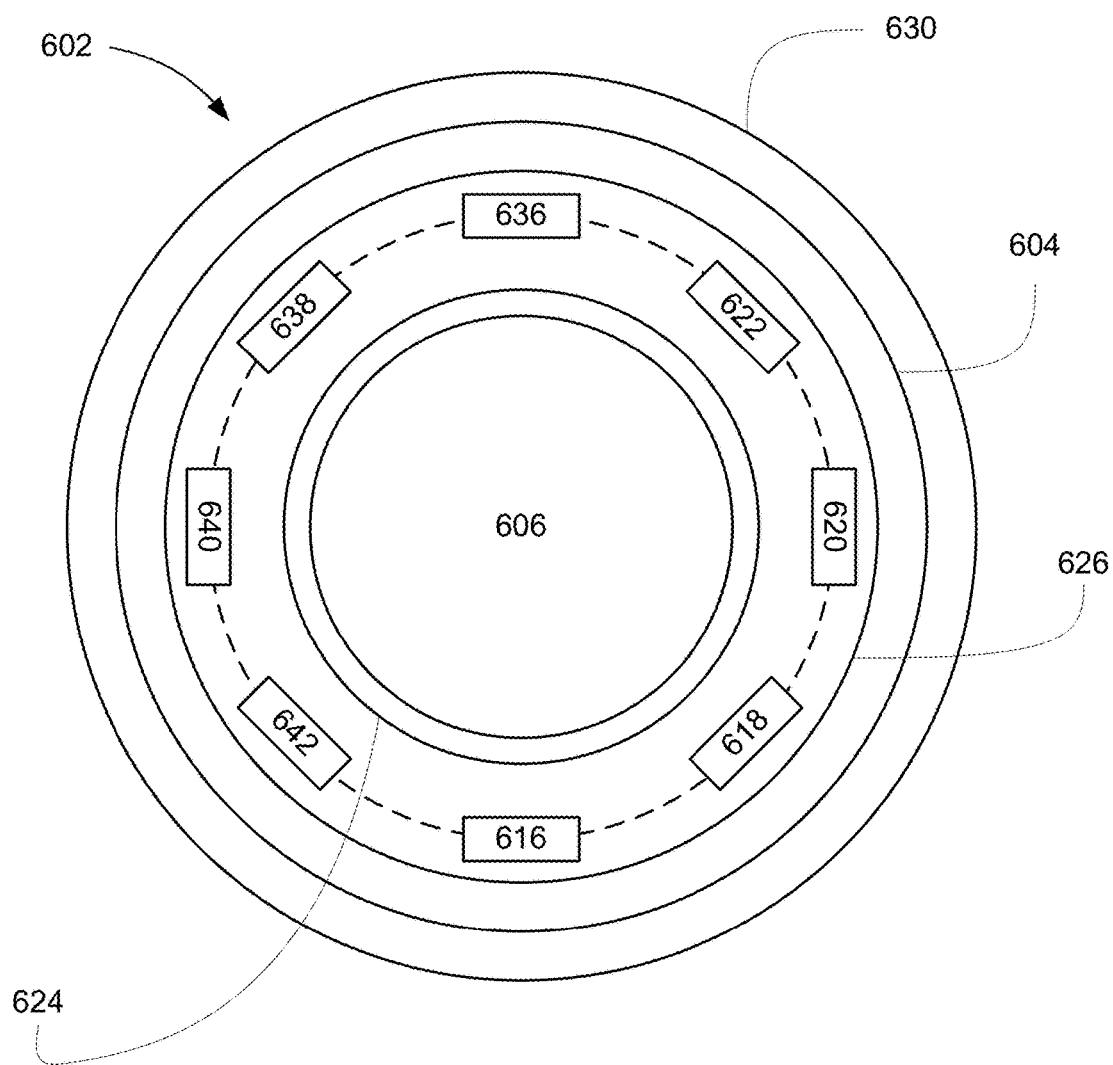
FIG. 10 is a schematic transverse cross-sectional view near the distal end of the balloon catheter illustrated in FIGS. 9A and 9B.

FIG. 10 is a transverse cross-sectional view near the distal end of a sensing balloon catheter similar to sensing balloon and catheter 602 shown in FIGS. 9A and 9B, but having eight splines with eight electrodes. The distal end of sensing balloon catheter 602 includes a protective balloon sheath 630, balloon 604, spline sheath 626 (prior to retraction), eight electrodes (616, 618, 620, 622, 636, 638, 640, 642), central ring electrode 624, and shaft 606.

The protective balloon sheath 630 may protect the balloon 604 that is folded onto the rest of the assembly as the balloon is advanced to the native valve. Accordingly, the protective balloon sheath 630 may be retracted once the balloon is located in the native valve annulus.

As noted above, balloon 604 may be bonded at its distal end to shaft 606 and at its proximal end to the catheter handle, where the balloon may be filled with saline through a leur connector. The catheter shaft extends all the way up to the handle of the catheter and has the necessary mechanical properties to enable easy maneuverability of the device to the aortic valve annulus through the various access routes used during the TAVR procedure.

Figure 11:
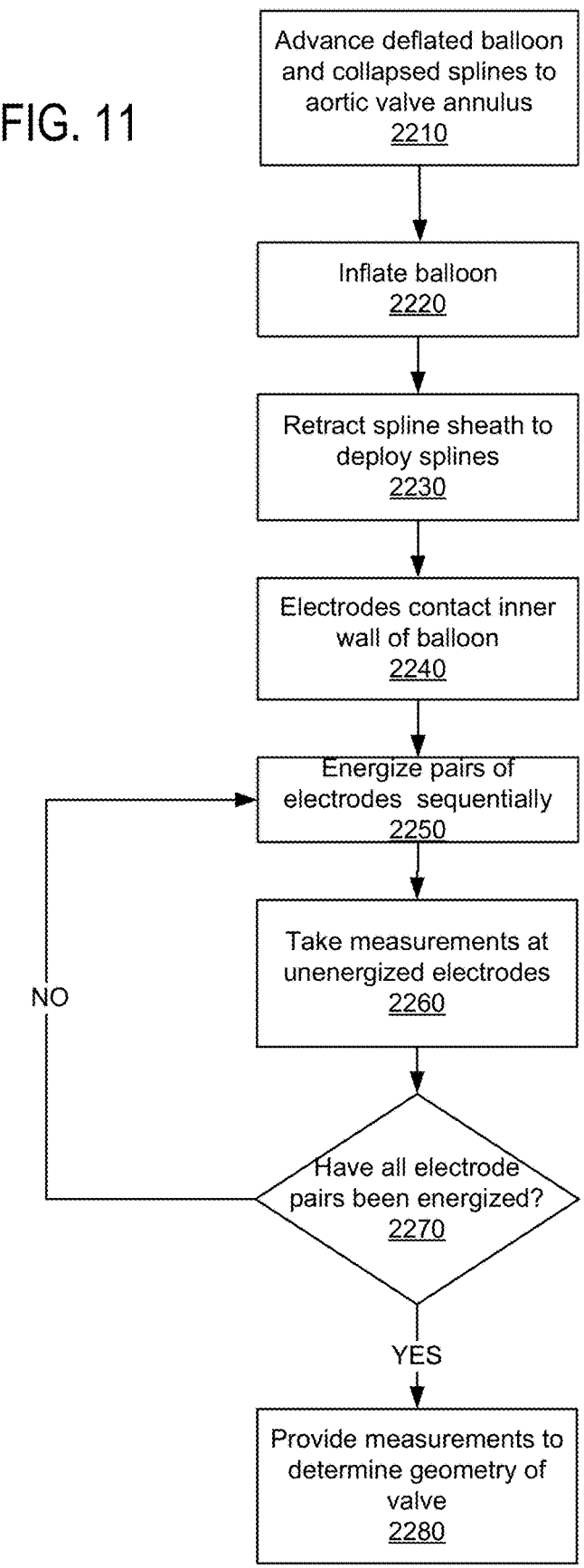
FIG. 11 is a flow chart depicting a method for determining the geometry of the native valve annulus according to aspects of the disclosure.

FIG. 11 is a flowchart depicting a method for assessing the major dimensions and eccentricity of an elliptical valve annulus where a transcatheter aortic valve according to the embodiments illustrated in FIGS. 9-10 is to be implanted.

In block 2210, the sensing balloon catheter, with the balloon in the deflated state and the splines in the collapsed state, may be advanced to the aortic valve annulus over a guide wire. In block 2220, the fluid lumen may be pressurized with a homogenous medium (e.g., saline) to inflate the balloon. The inflation fluid may exhibit homogenous conductivity of a known value as discussed above. As noted above, the compliance of the balloon is such that the inflated balloon conforms to the annulus of the native valve without altering the geometry of the annulus. Once the balloon is inflated, the spline sheath may be retracted in block 2230 to deploy and expand the splines. One of ordinary skill in the art would recognize the variety of techniques for sheath retraction. With the splines fully expanded, the electrodes thereon would contact the inner wall of the balloon in block 2240.

In block 2250, opposite electrode pairs (i.e., ({616,636}, {618,638}, {620,640}, {622,642}) may be energized sequentially. Referring to FIG. 10, electrode 616 and electrode 636 may be energized (i.e., driven) as the first electrode pair. For example, electrode 616 may be the source electrode and electrode 636 may be the sink electrode. When electrodes 616 and 636 are driven, the remaining electrodes (618, 620, 622, 638, 640, 642) may be non-driven or sense electrodes. As electrode 616 and electrode 636 are driven with a small drive current, an electric field is created in the saline environment inside the balloon similar to the techniques described above. The drive current may range from a few $\mu$A to a few mA. In this regard, the drive current depends on a variety of factors, including the homogenous medium used to inflate the balloon, the signal-to-noise ratio, temperature, etc. According to some embodiments, the balloon is made from an electrically insulative material. Thus, the generated electrical field may be well controlled within the balloon. Additionally, the balloon may act to block out electrical interference generated within the patient's body. Accordingly, the sensing electrodes (618, 620, 622, 638, 640, 642) may measure the voltage generated by the electrical field in block 2260.

In block 2270, a determination may be made as to whether each pair of electrodes has been driven. If not, the method returns to block 2250 to drive another pair (i.e., {618,638}) of electrodes. For example, electrode 618 and electrode 638 may be driven and the electric field generated may be measured at the sensing electrodes (616, 620, 622, 624, 636, 640, 642). The process may be repeated to drive each pair of electrodes. Referring to FIG. 10, eight electrodes would include four electrode pairs. Thus, driving the electrode pairs and measuring the electric field at the sensing electrodes may be performed four times. Accordingly, the driving of electrode pairs may occur more frequently or less frequently depending on whether fewer or more electrodes are used.

Once all of the electrode pairs have been energized, the process proceeds to block 2280, at which the measurements detected at the sensing electrodes may be used to determine the geometry of the native valve annulus. For instance, the major axis diameter (a), minor axis diameter (b), and eccentricity (b/a) of the annulus may be determined from the voltage measurements as the electric fields are generated and, hence, the voltages measured at the sense electrodes may be a function of the geometry of the cross-section. In some embodiments, the measurements may be provided to a trained statistical model to determine the dimensions of the valve annulus as discussed in greater detail below.

Figure 12:
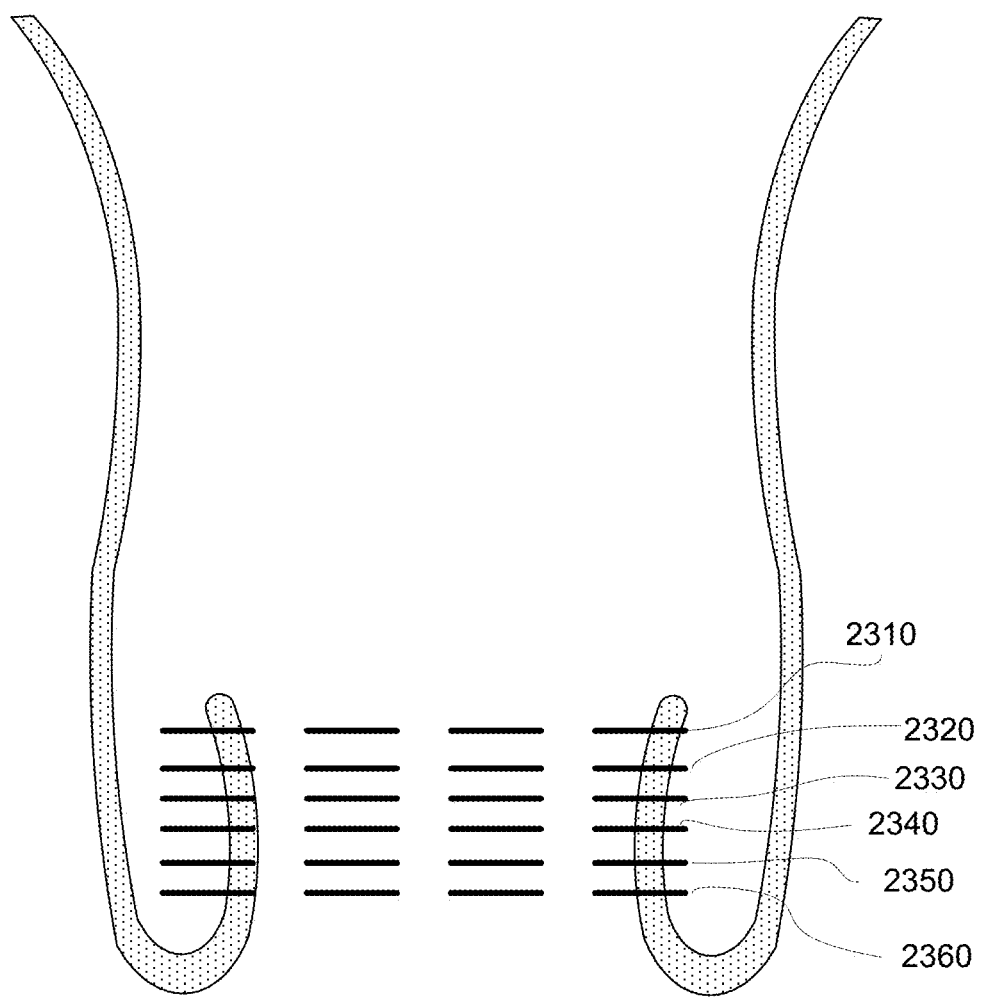
FIG. 12 is a diagrammatic view illustrating an example of determining the three-dimensional geometry of a native valve annulus according to aspects of the disclosure.

Additionally, the balloon sensing catheter may be used to obtain three-dimensional information about the native valve annulus. Referring to FIG. 12, a cross-section of a native valve is shown. Three-dimensional information for the valve may be constructed by re-deploying the balloon sensing catheter at different planes (2310, 2320, 2330, 2340, 2350, 2360). For example, the method depicted in FIG. 11 may be performed at a first plane 2310. Because the electrodes are radiopaque, positioning the balloon sensing catheter and deploying the splines may be accomplished using fluoroscopic guidance. The method may be repeated at each of the remaining planes (e.g., 2320, 2330, 2340, 2350, 2360.) The information gathered at each plane may be collated to develop three-dimensional information for the valve. The three-dimensional information may be used to decide the best landing spot for a prosthetic valve, thereby minimizing paravalvular leaks when an appropriately sized transcatheter valve is used. Three-dimensional information may be depicted graphically or numerically, depending on the needs to the user.

Figure 13:
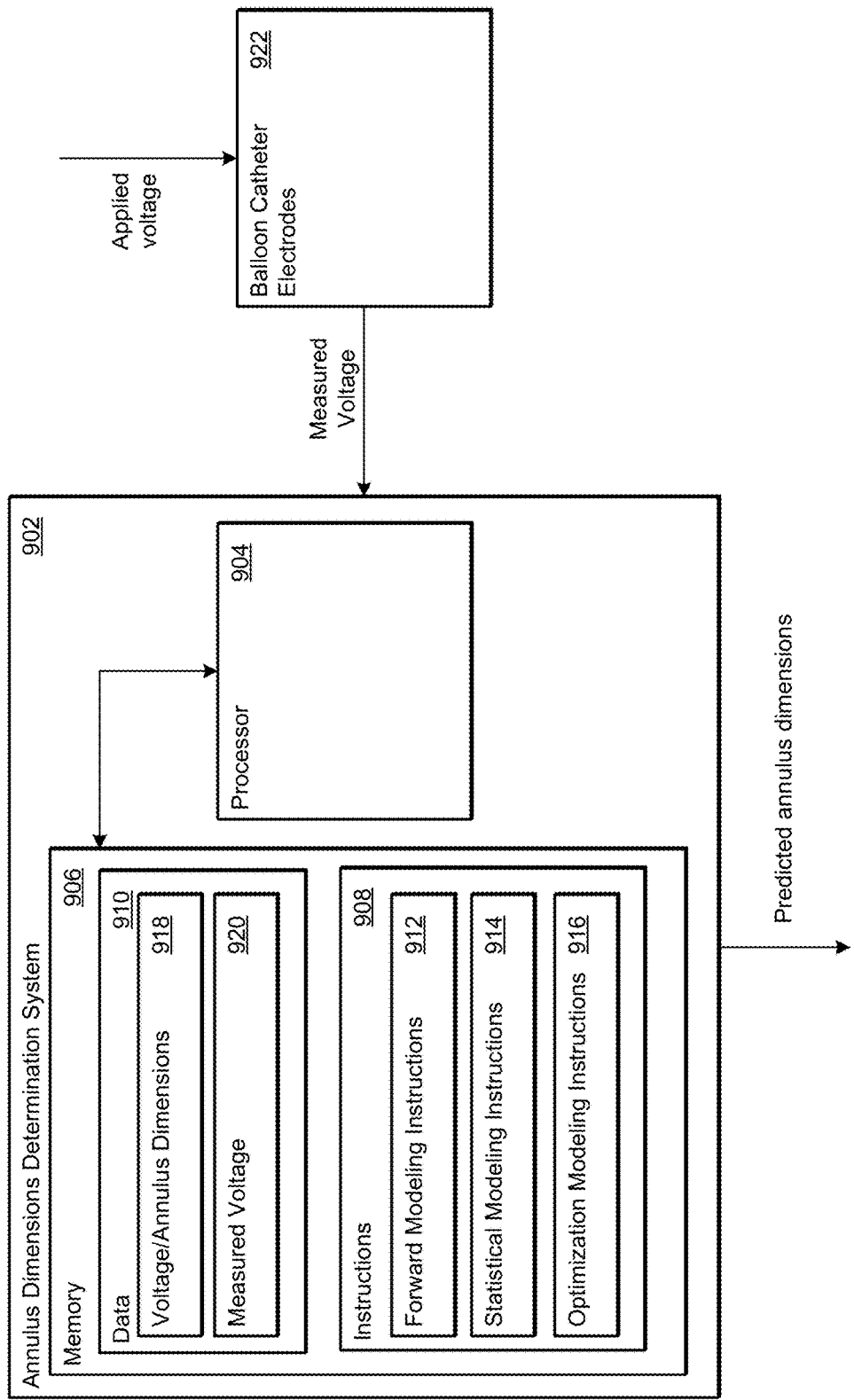
FIG. 13 is a block diagram illustrating an exemplary system for determining the dimensions of a native valve annulus according to aspects of the disclosure.

FIG. 13 illustrates an exemplary system 902 for determining the dimensions of a native valve annulus according to aspects of the disclosure. The system 902 may include a processor 904, a non-transitory, computer-readable memory 906, and other components typically present in general purpose computers. The system 902 may be a personal computer, intended for use by a user, having all the components normally found in a personal computer such as a central processing unit (CPU), display device, CD-ROM, hard drive, user inputs, speakers, modem and/or network interface device, and all of the components used for connecting these elements to one another. The system 902 may be in communication with one or more balloon catheter electrodes 922 and may receive one or more voltage measurements and/or current measurements from the one or more balloon catheter electrodes 922.

The processor 904 may be any conventional processor, such as commercially available CPUs. Alternatively, the processor 904 may be a dedicated device such as an ASIC or other hardware-based processor. Although FIG. 13 functionally illustrates the processor 904, memory 906, and other elements of the system 902 as being within the same block, the processor 904, system 902, or memory 906 may include multiple processors, computers, or memories that can or cannot be stored within the same physical housing. For example, the memory 906 may be any type of memory capable of storing information accessible by the processor 904, such as a hard-drive, memory card, ROM, RAM, DVD, CD-ROM, write-capable, or read-only memory, located in a housing different from that of the system 902. Accordingly, references to a processor, computer, or memory will be understood to include references to a collection of processors, computers, or memories that may or may not operate in parallel.

The memory 906 of the system 902 may store information accessible by the processor 904, including instructions 908 that may be executed by the processor 904. The instructions 908 can be any set of instructions to be executed directly, such as machine code, or indirectly, such as scripts, by the processor. In that regard, the terms "instructions," "application," "steps" and "programs" can be used interchangeably herein. The instructions 908 may be stored in object code format for direct processing by the processor 904, or in any other computer language including scripts or collections of independent source code modules that are interpreted on demand or compiled in advance. Functions, methods and routines of the instructions 908 are explained in more detail below.

The memory 906 may also include data 910 that may be retrieved, manipulated or stored by the processor 904. The data 910 may be retrieved, stored or modified by processor 904 in accordance with the instructions 908. For instance, although the subject matter described herein is not limited by any particular data structure, the data 910 may be stored in computer registers, in a relational database as a table having many different fields and records, or in one or more XML documents. The data 910 may also be formatted in any computer-readable format such as, but not limited to, binary values, ASCII or Unicode. Moreover, the data 910 may comprise any information sufficient to identify the relevant information, such as numbers, descriptive text, proprietary codes, pointers, references to data stored in other memories such as at other network locations, or information that is used by a function to calculate the relevant data.

As an initial step in predicting or estimating the dimensions for a given native valve annulus, a forward model may be developed using known valve annulus cross-sections. In this regard, the forward model may be developed using a plurality of mock annuluses with known cross-sectional dimensions. Simulating the native valve annulus using mock annuluses may include establishing one or more dimensions for the mock annulus, including the length of a major axis, the length of a minor axis, and the rotational angle of the balloon catheter relative to the mock valve annulus.

For example, a catheter may be deployed inside a compliant balloon that is inflated within several mock elliptical annuluses, each with known major axis and minor axis dimensions. Impedance data may be collected for each mock annulus to develop the forward model, which may correlate the relationship between the measured impedance values and the annulus dimensions. The empirical dimensional information collected from the measurements of the mock annuluses may be used to train predictive statistical models. Physics based computer models can also be used to formulate predictive models based on optimization techniques. For instance, the impedance data and the dimensional information of the mock annuluses may be correlated and simulated using one or more computer models to create the forward model. Accordingly, the forward model may be stored in the data 910 as the voltage/annulus dimension data 918. The forward model may then be used to estimate dimensions of annuluses with unknown-cross sections when voltage measurements for those annuluses are known. In particular, the forward model may be used to predict dimensional information for unknown geometries in patients.

Figure 14:
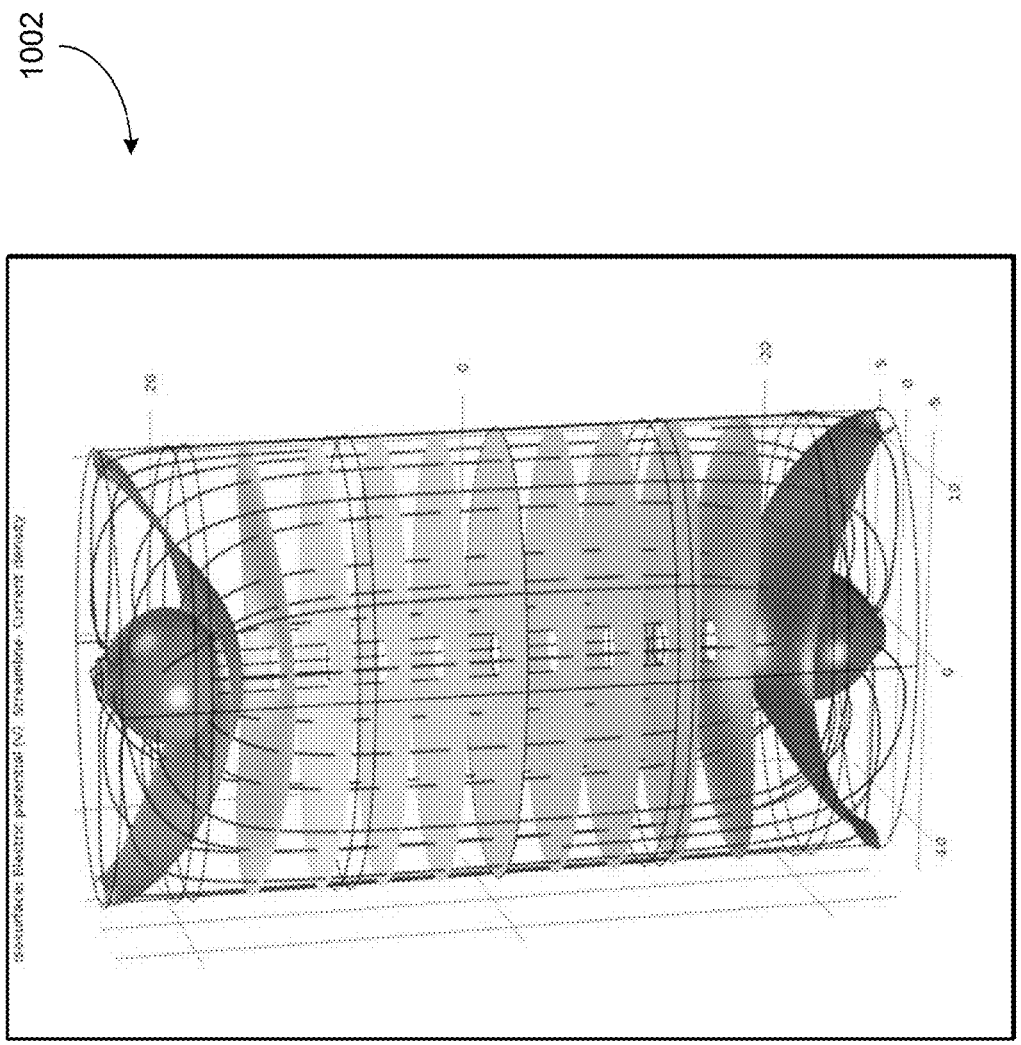
FIG. 14 is a highly schematic view illustrating simulated electrical fields produced from a forward model of a native valve annulus according to aspects of the disclosure.

FIG. 14 illustrates an example of simulated electrical fields produced by a forward model 1002 of a native valve annulus when the forward modeling instructions 912 are executed. The example shows the voltage distribution when the additional circumferential drive electrodes R1,R2 are energized. In one embodiment, the forward model may be developed using the COMSOL Multiphysics software, which is available from COMSOL, Inc. The forward model may be developed by simulating the electric voltage distribution inside balloons inflated in known annulus cross-sections. Alternatively, or in addition, the forward model may be developed using empirical data by measuring voltages/impedances at sense electrodes when the balloon is deployed in physical annulus geometries with known dimensions. The forward model may also be developed using any technique for evaluating the governing partial differential equation. This may include using the COMSOL Multiphysics software and does not preclude other standard finite element, finite volume or boundary element techniques, such as those described in U.S. Pat. No. 5,553,611 and U.S. Pat. No. 5,662,108, the disclosures of both of which are incorporated herein in their entireties.

Figure 15:
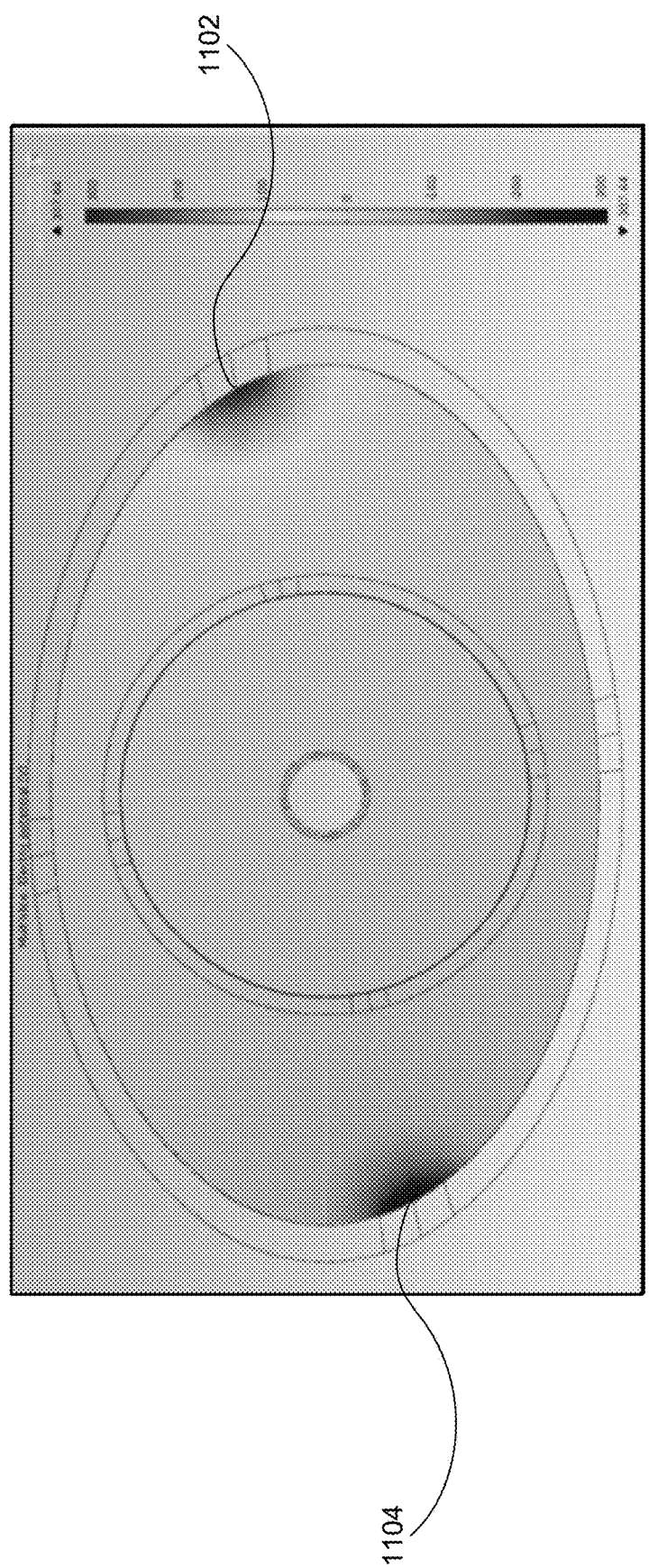
FIG. 15 is a transverse cross-sectional view schematically illustrating a simulated electrical field produced from a forward model of a native valve annulus according to aspects of the disclosure.
Figure 16:
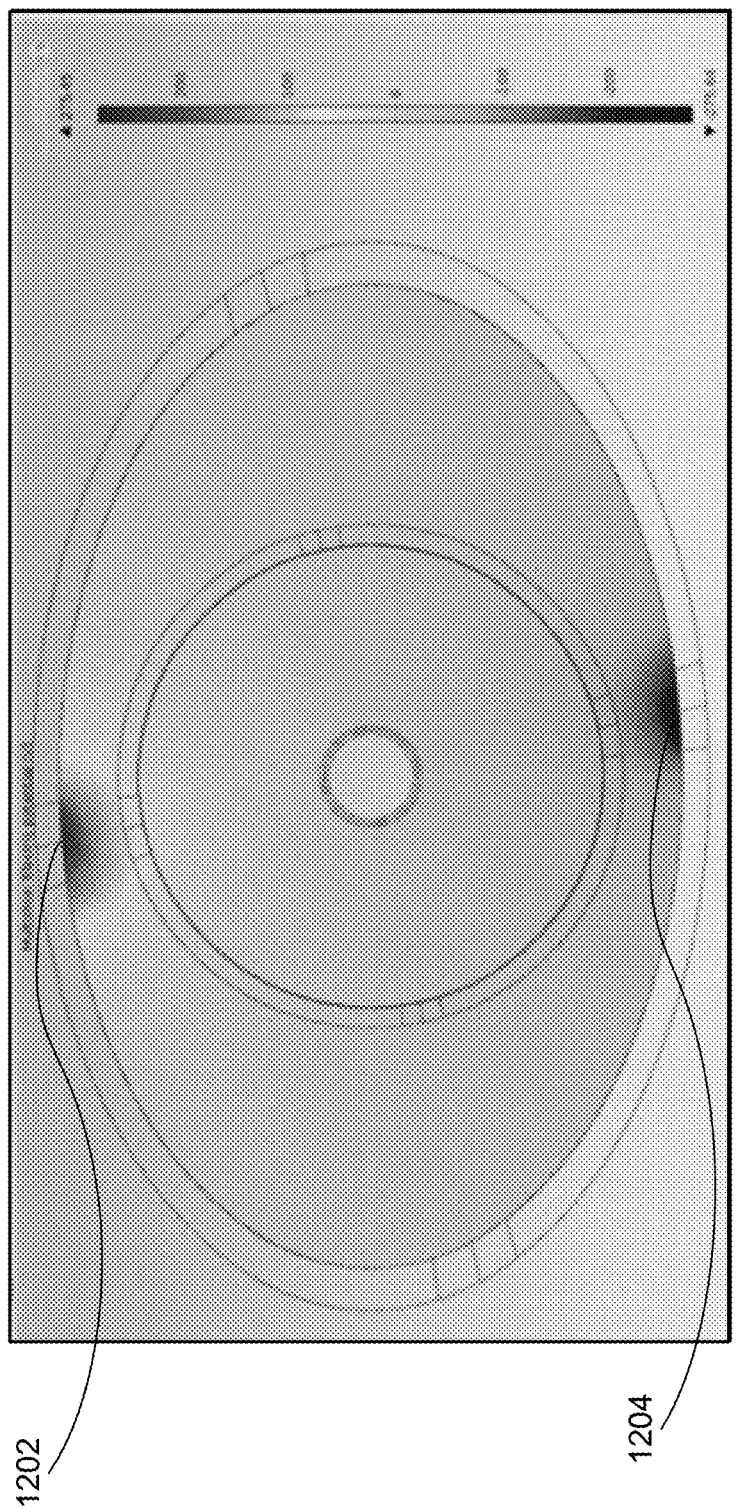
FIG. 16 is a transverse cross-sectional view schematically illustrating another simulated electrical field produced from the same forward model as was used for producing FIG. 17.

FIGS. 15-16 illustrate examples of simulated electrical voltages from the forward model of a valve annulus when different pairs of drive electrodes are energized. In particular, FIGS. 15-16 show the voltage distribution on a 2-dimensional slice representing the valve annulus. The dimensions of the simulated valve annulus are a length of the major axis (a) of 25 mm, a length of the minor axis (b) of 15 mm, and an angle, theta ($\theta$), of the simulated balloon catheter relative to the simulated valve annulus of 12°.

With reference to FIG. 15, this figure illustrates an example in which simulated drive electrodes B1,B3 are energized, where spot 1102 indicates a simulated voltage near the source electrode B1 and spot 1104 indicates a simulated voltage near the sink electrode B3. FIG. 16 illustrates an example in which simulated drive electrodes B2, B4 are energized, where spot 1202 indicates a simulated voltage near the source electrode B2 and spot 1204 indicates a simulated voltage near the sink electrode B4.

The instructions 912 for the forward model of the valve annulus may be performed a number of times with varying cross-sectional dimensions covering the physiological range of values expected in patients. Typically, the dimensions for the aortic valve annulus range between about 15 mm and about 30 mm on the major axis and between about 15 mm and about 30 mm on the minor axis in most patients and the instructions 912 for the forward model may be executed 300 to 400 times to accommodate these ranges.

When a baseline of simulated valve annulus dimensions and corresponding mathematically determined voltages have been established (i.e., stored as the voltage/dimension data 918), the computed voltages and corresponding cross-sectional dimensions may then be used as input to train a statistical model of the valve annulus. Alternatively, re-evaluations of the forward model may be used instead of, or in addition to, the trained statistical model. Similar to the techniques described above, the trained statistical model may be developed using a plurality of mock annuluses with known cross-sectional dimensions. Simulating the native valve annulus using mock annuluses may include establishing one or more dimensions for the mock annulus, including the length of a major axis, the length of a minor axis, and the rotational angle of the balloon catheter relative to the mock valve annulus.

For example, a catheter may be deployed inside a compliant balloon that is inflated within several mock elliptical annuluses, each with known major axis and minor axis dimensions. Impedance data may be collected for each mock annulus to develop the trained statistical model, which may correlate the relationship between the measured impedance values and the annulus dimensions. The empirical dimensional information collected from the measurements of the mock annuluses may be used to create the trained statistical model. Physics based computer models can also be used to formulate the trained statistical model based on optimization techniques. For instance, the impedance data and the dimensional information of the mock annuluses may be correlated and simulated using one or more computer models to create the trained statistical model. Accordingly, the trained statistical model may be stored in memory and, subsequently, used to estimate dimensions of annuluses with unknown-cross sections when voltage measurements for those annuluses are known. In particular, the trained statistical model may be used to predict dimensional information for unknown geometries in patients. The statistical model and the optimization model may be created during the manufacturing of the device, for example, as part of the calibration process.

The statistical model may determine the likelihood that a given voltage corresponds to a particular cross-sectional dimension, and based on this likelihood, provides an estimate of a cross-sectional dimension that a native valve annulus may have when given a measured voltage. Accordingly, the instructions 908 may include statistical modeling instructions 914 for training a statistical model based on the results from the forward model.

In particular, the input to the statistical model may include the changes in detected current or voltage between one or more of the sense electrodes S1-S4. Thus, the input to the statistical model may include:

$\Delta Z_x$, where $\Delta Z_x$ is the difference in impedance/voltage measured between S1 and S3, when current is driven between B1 and B3;

$\Delta Z_x'$, where $\Delta Z_x'$ is the difference in impedance/voltage measured between S1 and S3 when current is driven between B4 and B2;

$\Delta Z_y$, where $\Delta Z_y$ is the difference in impedance/voltage measured between S4 and S2 when current is driven between B4 and B2; and $\Delta Z_y'$, where $\Delta Z_y'$ is the difference in impedance/voltage measured between S4 and S2 when current is driven between B1 and B3.

In determining the various dimensions (i.e., major axis length, minor axis length, and orientation angle (θ)), the statistical model may use the following the equations:

$\mathrm{Sqrt}(a) = 12.28520 + (3.30140\mathrm{E}\text{-}003 * \Delta Zx) - (0.095653 * \Delta Zy) - (9.08522 * \Delta Zx') + (3.58041 * \Delta Zy') - (11.91111 * \Delta Zx / \Delta Zy) + (5.39767\mathrm{E}\text{-}003 * \Delta Zx * \Delta Zy) - (0.17402 * \Delta Zx * \Delta Zx') + (0.18097 * \Delta Zx * \Delta Zy') - (0.086074 * \Delta Zx * \Delta Zx / \Delta Zy) + (0.14963 * \Delta Zy * \Delta Zx') - (0.12923 * \Delta Zy * \Delta Zy') - (0.24691 * \Delta Zx' * \Delta Zy') + (4.83153 * \Delta Zx' * \Delta Zx / \Delta Zy) - (2.03900\mathrm{E}\text{-}003 * (\Delta Zy)^2) - (0.15075 * (\Delta Zx')^2) + (0.46870 * (\Delta Zy')^2) + (6.15900 * \Delta Zx / (\Delta Zy)^2);$ $(b)^{-2} = +6.51140\mathrm{E}\text{-}003 - (1.04237\mathrm{E}\text{-}003 * \Delta Zx) + (4.66057\mathrm{E}\text{-}004 * \Delta Zy) - (0.023578 * \Delta Zx') + (7.45789\mathrm{E}\text{-}003 * \Delta Zy') - (0.010474 * \Delta Zx / \Delta Zy) + (4.91274\mathrm{E}\text{-}005 * \Delta Zx * \Delta Zy) - (5.84344\mathrm{E}\text{-}004 * \Delta Zx * \Delta Zx') + (2.12512\mathrm{E}\text{-}004 * \Delta Zx * \Delta Zy') + (6.88946\mathrm{E}\text{-}004 * \Delta Zx * \Delta Zx / \Delta Zy) + (7.10642\mathrm{E}\text{-}004 * \Delta Zy * \Delta Zx') - (3.26035\mathrm{E}\text{-}004 * \Delta Zy * \Delta Zy') + (5.35515\mathrm{E}\text{-}004 * \Delta Zx' * \Delta Zy') + (0.012370 * \Delta Zx' * \Delta Zx / \Delta Zy) + (3.09055\mathrm{E}\text{-}003 * \Delta Zy' * \Delta Zx / \Delta Zy) - (2.93824\mathrm{E}\text{-}005 * (\Delta Zx)^2) - (1.82374\mathrm{E}\text{-}005 * (\Delta Zy)^2) - (8.98019\mathrm{E}\text{-}004 * (\Delta Zx')^2) + (3.70879\mathrm{E}\text{-}004 * (\Delta Zy')^2) + (4.19635\mathrm{E}\text{-}003 * \Delta Zx / (\Delta Zy)^2);$ and $\cos(\theta) * 1.44 = +25.25818 + (4.99918 * \Delta Zx) - (2.55078 * \Delta Zy) + (27.81105 * \Delta Zx') - (2.19657 * \Delta Zy') - (43.85162 * \Delta Zx / \Delta Zy) - (0.12290 * \Delta Zx * \Delta Zy) + (0.34645 * \Delta Zx * \Delta Zx') + (0.34743 * \Delta Zx * \Delta Zy') - (2.45659 * \Delta Zx * \Delta Zx / \Delta Zy) - (0.68657 * \Delta Zy * \Delta Zx') + (0.99559 * \Delta Zx' * \Delta Zy') - (11.20874 * \Delta Zx' * \Delta Zx / \Delta Zy) - (14.45341 * \Delta Zy' * \Delta Zx / \Delta Zy) + (0.062664 * (\Delta Zx)^2) + (0.060733 * (\Delta Zy)^2) - (0.96460 * (\Delta Zy')^2) + (19.23559 * \Delta Zx / (\Delta Zy)^2).$ In one embodiment, the foregoing equations may be derived using statistical modeling software available under the trademark Design-Expert® from Stat-Ease, Inc. of Minneapolis, Minn. Although shown with specific coefficients, the equations may be different depending on the inputs.

In one embodiment, training the statistical model may include providing a predetermined amount of input from the forward model, such as 300-400 sets of data, where one set of data may include the voltage measurements from the sense electrodes and the known dimensions of the simulated valve annulus. Accordingly, it should be understood that the foregoing equations may vary depending on the number of data sets provided to the statistical model and the baseline measurements used in developing the forward model.

Once trained, the statistical model may provide an initial prediction of the dimensions of a native valve annulus having an unknown cross-section. For example, the sensing balloon catheter may be inserted into the native valve annulus, the voltage measurements may be acquired from the inserted sensing balloon catheter (and stored as measured voltage data 920), and the acquired voltage measurements may then be provided to the statistical model. The initially predicted measurements from the statistical model may then be provided to an optimization model for determining refined dimensional estimates of the valve annulus having the unknown cross-section (i.e., best-fit dimensional estimates). Accordingly, the instructions 908 may include optimization modeling instructions 916 for determining an optimized set of dimensions of the unknown cross-section of the native valve annulus given a set of predicted (i.e., estimated) dimensions from the statistical model. In one embodiment, the optimization model of the optimization modeling instructions 916 uses a Nelder-Mead optimization algorithm.

Figure 17:
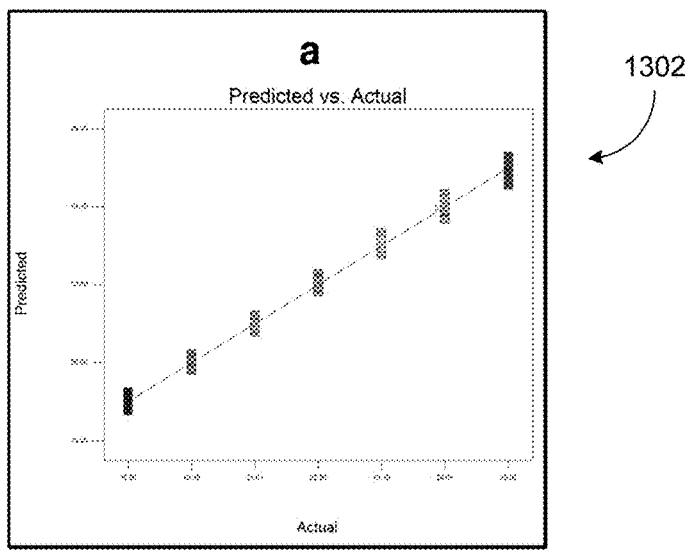
FIGS. 17-19 are graphs comparing predicted native valve annulus dimensions with the actual valve annulus dimensions according to aspects of the disclosure.
Figure 18:
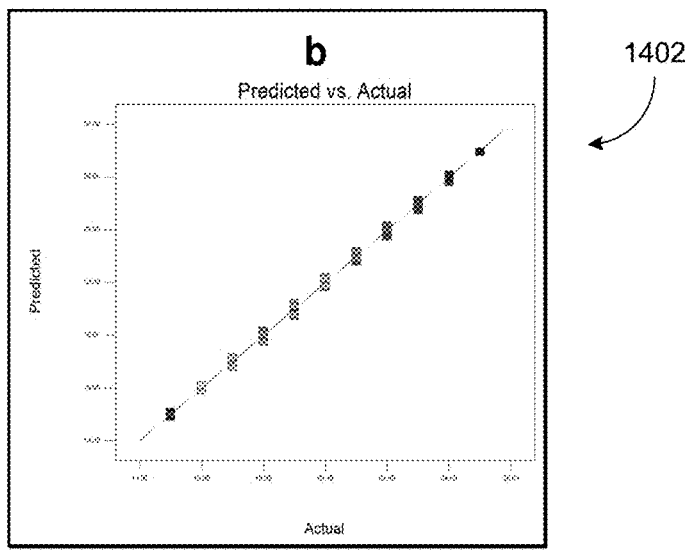
Figure 19:
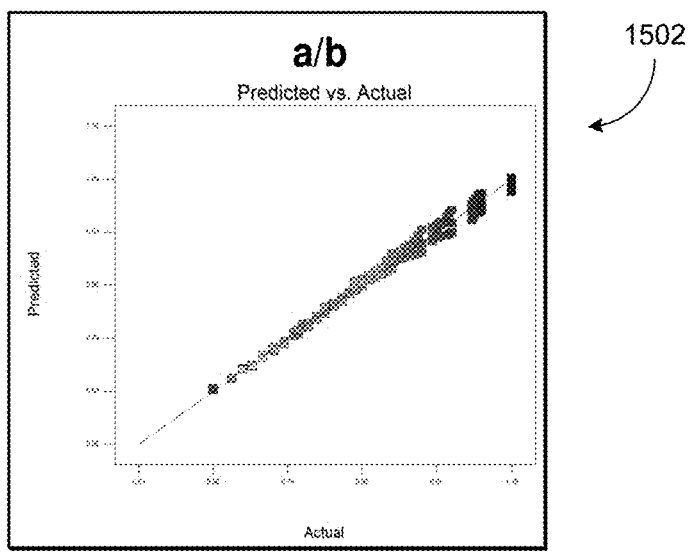

FIGS. 17-19 are graphs 1302, 1402, 1502 comparing a predicted valve annulus dimension obtained from the trained statistical model with the actual dimensions of a simulated valve annulus. In particular, FIG. 17 is a graph 1302 comparing a predicted length of the major axis (a) with the known length of the major axis of a simulated valve annulus; FIG. 18 is a graph 1402 comparing a predicted length of the minor axis (b) with the known length of the minor axis of the simulated valve annulus; and FIG. 19 is a graph 1502 comparing a predicted eccentricity (a/b) with the known eccentricity of the simulated valve annulus. As each of the graphs 1302/1402/1502 is relatively linear with a high coefficient of determination ($R^2$) value, it is clear that the disclosed systems and methods can provide a highly accurate estimate of the dimensions of a valve annulus.

To further highlight the accuracy of the disclosed systems and methods, Table 1 shows a comparison of a simulated valve annulus having known dimensions with predicted dimensions obtained from (a) using the statistical model, and (b) using the output from the statistical model as input to the optimization model.

TABLE 1

| Actual Dimensions | | | Statistical Model Prediction | | | Optimization Model Prediction | | |
|---|---|---|---|---|---|---|---|---|
| a (mm) | b (mm) | θ (mm) | a (mm) | b (mm) | Θ (mm) | a (mm) | b (mm) | θ (mm) |
| 25 | 20 | 22.5 | 25.09 | 19.87 | 37.18 | 24.99 | 20.00 | 22.49 |
| 23 | 22 | 60 | 23.04 | 22.00 | 50.71 | 22.99 | 22.00 | 59.92 |
| 22.5 | 22.5 | 40 | 22.65 | 22.41 | 44.05 | 22.5 | 22.5 | 40.04 |
| 21.7 | 18.1 | 70 | 21.49 | 18.21 | 69.26 | 21.69 | 18.10 | 70.05 |
| 24.8 | 15.6 | 12 | 24.87 | 15.48 | 22.10 | 24.80 | 15.59 | 12.08 |

As can be seen from Table 1, the predicted dimensions of the simulated valve annulus are highly accurate when compared with the actual dimensions of the simulated valve annulus.

Figure 20:
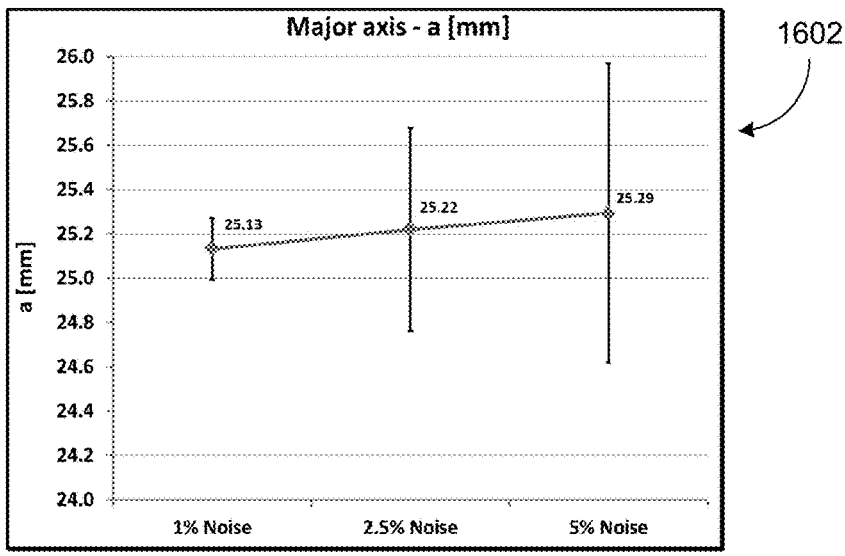
FIGS. 20-22 are graphs showing predicted valve annulus dimensions with Gaussian noise introduced to the voltage measurements according to aspects of the disclosure.
Figure 21:
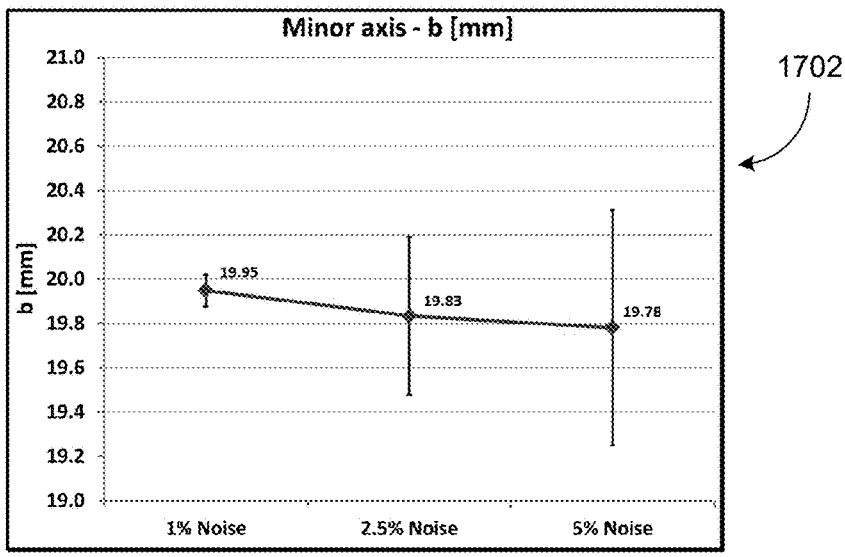
Figure 22:
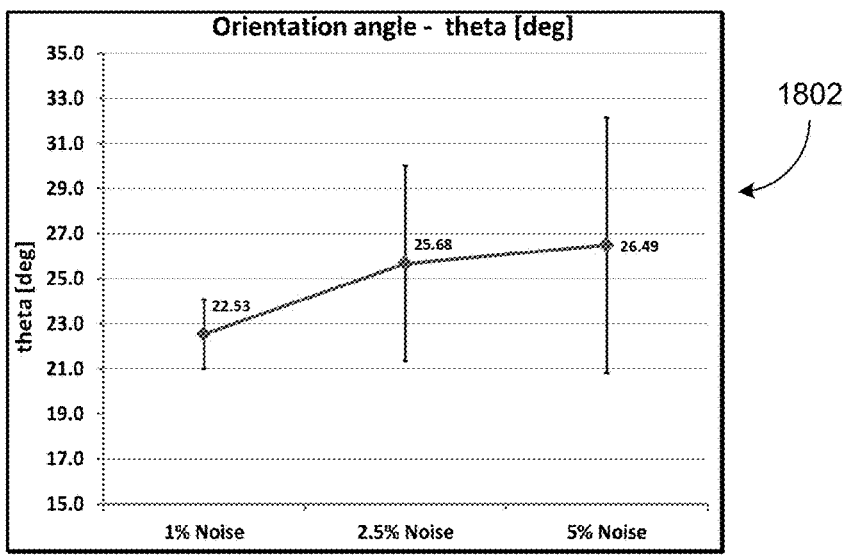

The foregoing system was also tested under noisy conditions. In particular, the test was done on data that corresponded to the length of a major axis (a) of 25 mm, the length of a minor axis (b) of 20 mm, and an angle, theta (θ), of a simulated balloon catheter relative to a simulated valve annulus of 22.5°. The test included introducing 1%, 2.5%, and 5% Gaussian noise to the simulated voltage values. FIGS. 20-22 are graphs 1602, 1702, 1802 of the predicted valve annulus dimensions with the introduced Gaussian noise. Table 2 below further shows five separate predicted valve annulus dimensions (i.e., the output from the optimization model) where the valve annulus dimensions are known (i.e., a=25 mm, b=20 mm, and θ=22.5°) and where Gaussian noise was introduced in the simulated voltage measurements.

TABLE 2

| 1% Gaussian Noise | | | 2.5% Gaussian Noise | | | %5 Gaussian Noise | | |
|---|---|---|---|---|---|---|---|---|
| a (mm) | b (mm) | θ (mm) | a (mm) | b (mm) | θ (mm) | a (mm) | b (mm) | θ (mm) |
| 25.23 | 19.82 | 25.07 | 26.01 | 19.22 | 29.69 | 26.15 | 19.12 | 32.35 |
| 25.02 | 19.98 | 22.91 | 24.94 | 20.05 | 29.20 | 25.08 | 19.93 | 24.39 |
| 25.05 | 19.96 | 21.55 | 24.91 | 20.08 | 23.42 | 25.22 | 19.83 | 17.72 |
| 25.03 | 19.98 | 21.79 | 25.02 | 19.99 | 26.75 | 25.67 | 19.48 | 29.38 |
| 25.00 | 20.00 | 21.32 | 25.22 | 19.83 | 19.33 | 24.35 | 20.54 | 28.59 |

Table 2 shows that the disclosed system is relatively accurate even under conditions in which there may be noise in the measured voltages. Under real-world conditions, it is expected that there is about 1% of Gaussian noise in the measured voltages.

Furthermore, when used in real-world conditions, there may be an offset between the balloon catheter with the disclosed electrode arrangement and the axis of the valve annulus after deployment in the annulus. To account for such cases, the statistical model may be trained with known offsets using the forward model, and the output of the statistical model may be used as an initial prediction input to the disclosed optimization model. Under these circumstances, the disclosed systems and methods may be used to determine the offsets along with the determination of the annulus dimensions. For example, these offsets may include a longitudinal (i.e., x-axis) offset and a latitudinal (i.e., y-axis) offset of the sensing balloon catheter relative to the valve annulus.

Figure 23:
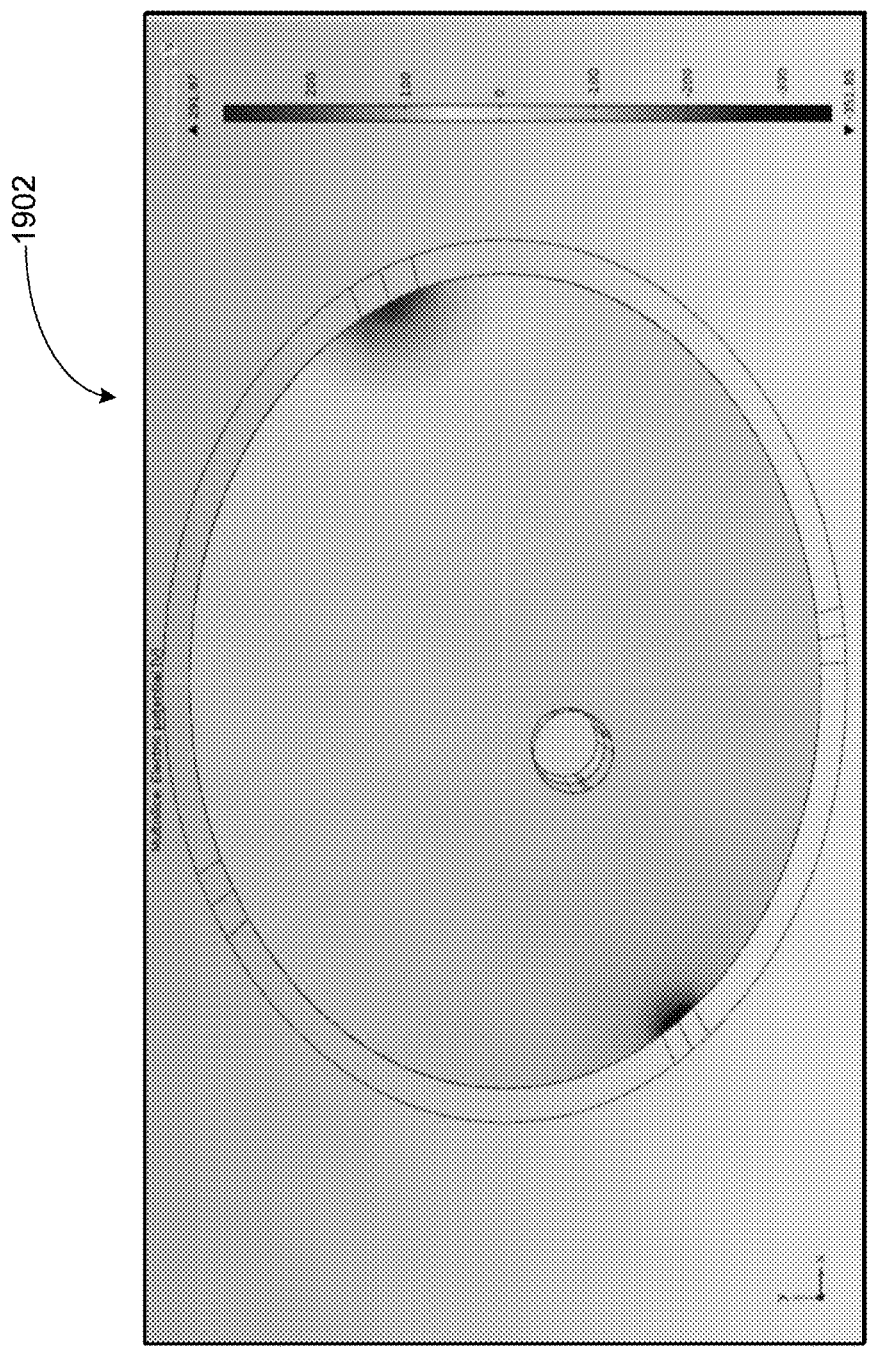
FIG. 23 is a transverse cross-sectional view schematically illustrating an electrical field simulated by the forward model of the native valve annulus with the balloon catheter inserted, wherein the balloon catheter was inserted with a known X-offset and a known Y-offset according to aspects of the disclosure.

FIG. 23 illustrates an example of a simulated electrical field 1902 of the forward model of the native valve annulus with a simulated balloon catheter being inserted at a known X-offset and a known Y-offset. Table 3 below shows the predicted dimensions of the forward model, including the X-offset and the Y-offset based on simulated voltage measurements, which were first provided to the statistical model of the valve annulus. The output of the statistical model was then provided as input to the optimization model to obtain the predicted dimensions of the forward model.

TABLE 3

| Actual Dimensions and Offsets | | | | | Predicted Dimensions and Offsets | | | | |
|---|---|---|---|---|---|---|---|---|---|
| a (mm) | b (mm) | θ (deg) | X offset (mm) | Y offset (mm) | a (mm) | b (mm) | θ (deg) | X offset (mm) | Y offset (mm) |
| 25 | 20 | 22.5 | 0 | 1 | 25.01 | 20 | 22.55 | −0.001 | 0.999 |
| 25 | 20 | 22.5 | −2.6 | −0.2 | 25.12 | 19.90 | 24.29 | −2.586 | −0.292 |
| 25 | 20 | 22.5 | 2 | 2 | 25.00 | 19.99 | 22.51 | 1.99 | 1.99 |

Figure 24:
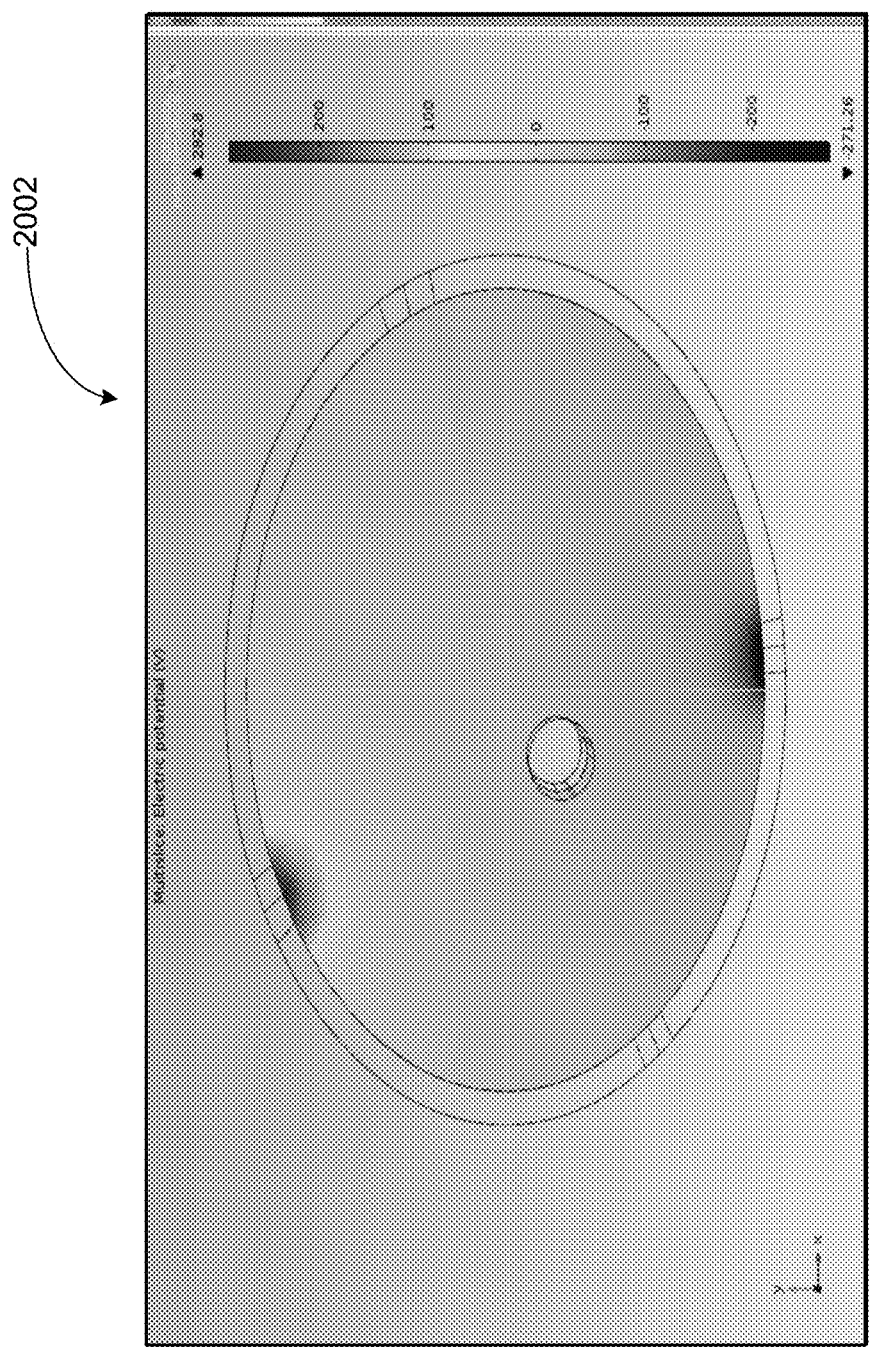
FIG. 24 is a transverse cross-sectional view schematically illustrating another electrical field simulated by the forward model of the native valve annulus with the balloon catheter inserted, wherein the balloon catheter was inserted with a known X-offset and a known Y-offset according to aspects of the disclosure.

FIG. 24 illustrates another example of a simulated electrical field 2002 of the forward model of the native valve annulus with a simulated balloon catheter being inserted at a known X-offset, a known Y-offset, and a known level of Gaussian noise. Table 4 below shows the predicted dimensions of the forward model, including the X-offset and the Y-offset, where the forward model has known dimensions (i.e., a=25 mm, b=20 mm, θ=22.5°), offsets (i.e., X-offset=2 mm, Y-offset=2 mm), and Gaussian noise level (i.e., 5%). The predicted dimensions were obtained by providing simulated voltage measurements to the statistical model, and then providing the output of the statistical model to the optimization model.

TABLE 4

| | Predicted Dimensions and Offsets | | | | |
|---|---|---|---|---|---|
| | a (mm) | b (mm) | θ (deg) | X-offset (mm) | Y-offset (mm) |
| | 24.84 | 20.13 | 28.64 | 1.72 | 2.25 |
| | 23.52 | 21.26 | 25.18 | 1.84 | 2.36 |
| | 24.83 | 20.12 | 24.35 | 1.88 | 2.00 |
| | 24.92 | 20.07 | 25.07 | 1.82 | 2.03 |
| | 26.57 | 18.82 | 27.36 | 2.16 | 1.99 |
| Mean | 24.94 | 20.08 | 26.12 | 1.88 | 2.13 |
| SD | 1.08 | 0.86 | 1.80 | 0.17 | 0.17 |

Figure 25:
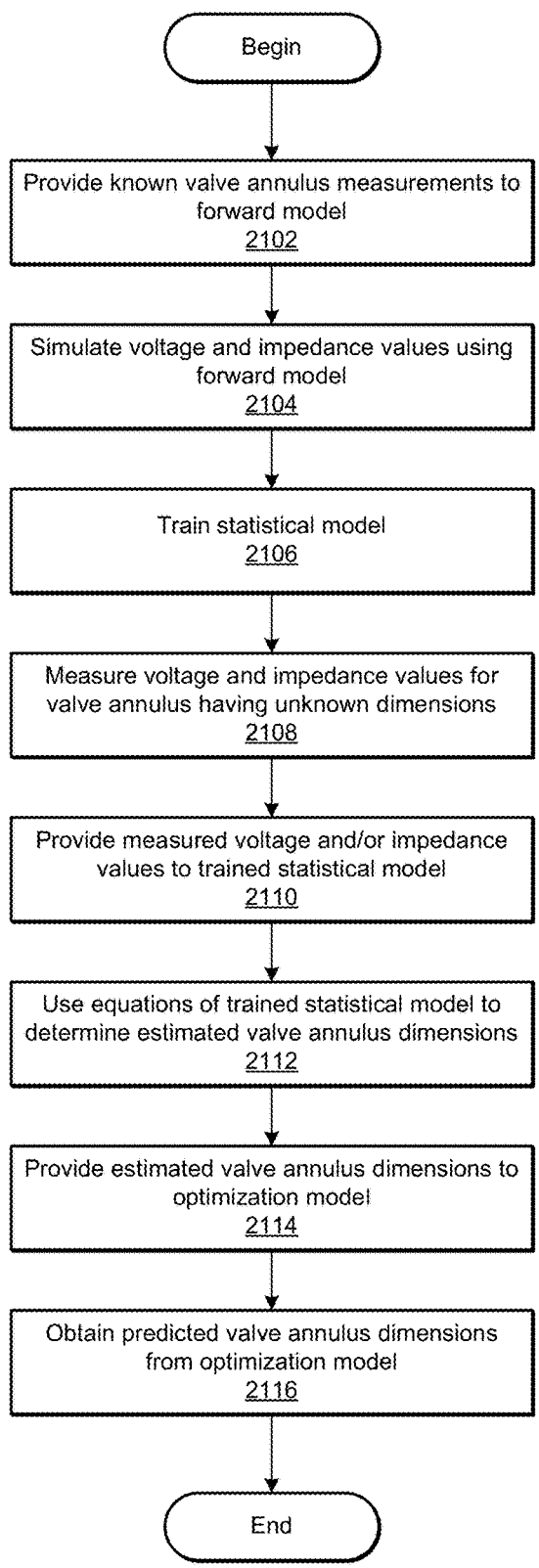
FIG. 25 is a flowchart depicting an example of logic flow for determining the dimensions of the cross-section of a native valve annulus according to aspects of the disclosure.

FIG. 25 is a flowchart depicting an example of logic flow for determining the dimensions of a native valve annulus. As shown in FIG. 25, an initial set of valve annulus dimensions may be provided to a forward model of the valve annulus (Block 2102). Using the forward model, simulated electrical fields may be generated by simulated drive electrodes, and the voltage measurements determined from simulated sense electrodes may be stored (Block 2104).

Determining voltage measurements from the simulated valve annulus and simulated electrical fields may also include obtaining other electrical measurements, such as impedance values from the simulated sense electrodes. The determined voltage measurements, and other electrical measurements, may be stored with an association to corresponding known dimensions of the simulated valve annulus. Alternatively, or in addition, the forward model may be an in vitro experimental model where sense electrode measurements are stored when the balloon is deployed in the native valve annulus with known dimensions. Other data about the simulated valve annulus may also be associated with the obtained voltage measurements, such as an X-offset value, a Y-offset value, the orientation of the simulated valve annulus ellipse relative to the simulated balloon catheter, and other such values.

A statistical model may then be trained with the obtained measurements and the known dimensions of the simulated valve annulus corresponding to the obtained measurements (Block 2106). In one embodiment, the statistical model may be trained with a predetermined number of data sets, such as 300-400 data sets, where a data set includes the voltage measurements, any offset values, and the known dimensions of the simulated valve annulus. Once trained, the statistical model may be used to obtain an initial estimate of the dimensions of a native valve annulus having an unknown cross-section. In particular, and as discussed above, a balloon catheter having the aforementioned drive and sense electrodes may be inserted into the native valve annulus, one or more of the drive electrodes may then be energized, and the detected voltage at one or more corresponding sense electrodes may then be measured (Block 2108). The measured voltage values may then be provided to the trained statistical model. (Block 2110). The trained statistical model may invoke one or more determined equations, as discussed above, to determine estimated dimensions of the native valve annulus (Block 2112). Finally, the initial estimated dimensions of the native valve annulus may be provided to the optimization model (Block 2114), which may provide a prediction of the dimensions of the native valve annulus (Block 2116).

In this manner, the disclosed systems and methods provide a highly accurate prediction of the dimensions of a native valve annulus. As the disclosed balloon catheter may be used in conjunction with a non-compliant balloon catheter, the measurements for a native valve annulus may be obtained immediately after a valvuloplasty procedure, which may be more relevant for a prosthetic valve implantation than the valve annulus dimensions before valvuloplasty.

Furthermore, the disclosed systems and methods reduce the need for pre-procedural work before replacing a native valve with a prosthetic valve, and, because the measurements of the valve annulus are obtained as part of the valvuloplasty procedure, the patient's exposure to radiation is reduced. Moreover, the disclosed systems and methods reduce the total time of the valve replacement procedure, as no significant pre-procedural work is needed to determine the size of the annulus. In addition, as the materials involved are relatively inexpensive, the overall cost of the disclosed systems and methods is relatively minor compared with other techniques. Thus, the disclosed systems and methods present a marked advantage over the current state of the art with regard to valve annulus sizing.

A system for determining the dimensions and geometry of a native valve annulus for trans-catheter valve implantation, the system includes a balloon extending in a longitudinal direction and having an interior surface; a shaft extending in the longitudinal direction within the balloon; a first pair of electrodes on the interior surface of the balloon and configured to produce a first electrical field based on a first predetermined current; a second pair of electrodes on the interior surface of the balloon and configured to produce a second electrical field based on a second predetermined current; a first sense electrode pair on the shaft and configured to detect the first and second electrical fields; and a second sense electrode pair on the shaft and configured to detect the first and second electrical fields; and/or wherein the balloon is an insulative material such that the first electrical field and the second electrical field are confined to an area inside the balloon; and/or wherein the first sense electrode pair is at a midpoint of a length of the shaft within the balloon; and/or an electrode of the first pair of electrodes is positioned at an angle of about 90° in a circumferential direction of the balloon from an electrode of the second pair of electrodes; and the second sense electrode pair is positioned at an angle of about 90° in the circumferential direction of the balloon from the first sense electrode pair; and/or a third pair of electrodes on the shaft, one electrode of the third pair of electrodes being positioned a predetermined distance in a first direction along the shaft from the first sense electrode pair and the other electrode of the third pair of electrodes being positioned the predetermined distance in a second direction along the shaft from the first sense electrode pair, the second direction being opposite the first direction, the third pair of electrodes being configured to produce a third electrical field based on a third predetermined current; and a third sense electrode pair on the shaft and configured to detect the third electrical field.

A method for determining the dimensions and geometry of a native valve annulus for trans-catheter valve implantation that includes loading a balloon catheter in a delivery system, wherein the balloon catheter includes a balloon extending in a longitudinal direction and having an interior surface; a shaft extending in the longitudinal direction within the balloon; a first pair of drive electrodes on the interior surface of the balloon; a second pair of drive electrodes on the interior surface of the balloon; a first sense electrode pair on the shaft; and a second sense electrode pair on the shaft; delivering the balloon catheter to the native valve annulus; deploying the balloon catheter within the native valve annulus so that the balloon conforms to a surface of the native valve annulus; applying a first current to the first pair of electrodes to produce a first electrical field; applying a second current to the second pair of electrodes to produce a second electrical field; detecting the first electrical field with the first and second sense electrode pair; detecting the second electrical field with the first and second sense electrode pair; and determining one or more dimensions of the native valve annulus based at least on the detected first electrical field and the detected second electrical field; and/or wherein the balloon is an insulative material such that the first electrical field and the second electrical field are confined to an area inside the balloon; and/or wherein the first sense electrode pair is at a midpoint of a length of the shaft within the balloon; and/or wherein the electrodes that comprise the first and second pairs of drive electrodes are affixed about 180° apart on the interior surface such that the electrodes of the first and the second drive electrode pairs are about 90° degrees apart on the interior surface; and the electrodes that comprise the first and sense electrode pairs are affixed about 180° apart on the shaft such that the electrodes of the first and the second sense electrode pairs are about 90° apart on the shaft; and/or wherein the balloon catheter includes a third pair of electrodes on the shaft, one electrode of the third pair of electrodes being positioned a predetermined distance in a first direction along the shaft from the first sense electrode pair and the other electrode of the third pair of electrodes being positioned the predetermined distance in a second direction along the shaft from the first sense electrode pair, the second direction being opposite the first direction; and a third sense electrode pair on the shaft; and the method includes:

applying a third current to the third pair of electrodes to produce a third electrical field;

detecting the third electrical field with the third sense electrode pair; and further determining the one or more dimensions of the native valve annulus based at least on the detected third electrical field.

A system for determining the dimensions and geometry of a native valve annulus for trans-catheter valve implantation that includes a non-transitory, computer-readable medium comprising computer-executable instructions; and one or more processors in communication with the non-transitory, computer-readable medium that, when the computer-executable instructions are executed, are configured to receive first voltage values from a first sense electrode pair on a shaft of a balloon catheter, the first sense electrode pair being configured to detect a first electrical field produced by a first pair of drive electrodes and a second electrical field produced by a second pair of drive electrodes; receive second voltage values from a second sense electrode pair on the shaft of the balloon catheter, the second sense electrode pair being configured to detect the first electrical field and the second electrical field; determine a major axis length of the native valve annulus based on the first and second voltage values; determine a minor axis length of the native valve annulus based on the first and second voltage values; and determine an eccentricity of the native valve annulus based on the determined major axis length and the determined minor axis length; and/or wherein the one or more processors are further configured to:

determine an estimated major axis length of the native valve annulus by providing the first and second voltage values to a statistical model of the native valve annulus; and determine the major axis length of the native valve annulus by applying an optimization model of the native valve annulus to the estimated major axis length; and/or wherein the one or more processors are further configured:

determine at least one offset value associated with the balloon catheter based on the detected first and second electrical fields, wherein the at least one offset value identifies an amount of offset of an axis of the balloon catheter relative to an axis of the native valve annulus.

A method for determining the dimensions and geometry of a native valve annulus for trans-catheter valve implantation that includes receiving, with one or more processors, first voltage values from a first sense electrode pair on a shaft of a balloon catheter, the first sense electrode pair being configured to detect a first electrical field produced by a first pair of drive electrodes and a second electrical field produced by a second pair of drive electrodes; receiving, with the one or more processors, second voltage values from a second sense electrode pair on the shaft of the balloon catheter, the second sense electrode pair being configured to detect the first electrical field and the second electrical field; determining, with the one or more processors, a major axis length of the native valve annulus based on the first and second voltage values; determining, with the one or more processors, a minor axis length of the native valve annulus based on the first and second voltage values; and determining, with the one or more processors, an eccentricity of the native valve annulus based on the determined major axis length and the determined minor axis length; and/or determining, with the one or more processors, an estimated major axis length of the native valve annulus by providing the first and second voltage values to a statistical model of the native valve annulus; wherein the step of determining the major axis length of the native valve annulus includes applying an optimization model of the native valve annulus to the estimated major axis length; and/or determining, with the one or more processors, at least one offset value associated with the balloon catheter based on the received first and second voltage values, wherein the at least one offset value identifies an amount of offset of an axis of the balloon catheter relative to an axis of the native valve annulus; and/or A system for determining the dimensions and geometry of a native valve annulus for trans-catheter valve implantation that includes a balloon extending in a longitudinal direction; a shaft extending in the longitudinal direction within the balloon; a first spline connected to the shaft; a second spline connected to the shaft; a third spline connected to the shaft; a first electrode positioned on the first spline; a second electrode positioned on the second spline; and a sensing electrode positioned on the third spline; wherein the first electrode and the second electrode produce an electrical field that is detected by the sensing electrode; and/or a central ring electrode located on the shaft and configured to measure values associated with the electrical field produced by the first and second electrodes; and/or wherein the first electrode is a source electrode; and/or wherein the second electrode is a sink electrode.

A method for determining the dimensions and geometry of a native valve annulus for trans-catheter valve implantation that includes loading a balloon catheter in a delivery system, the balloon catheter includes a balloon extending in a longitudinal direction; a shaft extending in the longitudinal direction within the balloon; a plurality of splines connected to the shaft; a first pair of electrodes on a first pair of the splines; and a second pair of electrodes on a second pair of the splines; delivering the balloon catheter to the native valve annulus; deploying the balloon catheter at a first longitudinal position within the native valve annulus so that the balloon conforms to a surface of the native valve annulus at the first longitudinal position; deploying the plurality of splines so that the splines move radially outward from the shaft; applying a first current to the first pair of electrodes to produce a first electrical field; measuring, using the second pair of electrodes, values associated with the first electrical field; applying a second current to the second pair of electrodes to produce a second electrical field; measuring, using the first pair of electrodes, values associated with the second electrical field; and determining one or more dimensions of the native valve annulus based at least on the values associated with the first electrical field and the second electrical field; and/or wherein the balloon catheter also includes a central ring electrode located on the shaft, and the method further comprises:

measuring at the central ring electrode values associated with the first electrical field; and/or measuring at the central ring electrode values associated with the second electrical field; and/or wherein the balloon catheter includes a third pair of electrodes on a third pair of the plurality of splines; and the method further comprises:

applying a third current to the third pair of electrodes to produce a third electrical field;

measuring, using the first pair of electrodes and the second pair of electrodes, values associated with the third electrical field; and/or wherein the balloon catheter that includes a fourth pair of electrodes on a fourth pair of the plurality of splines; and the method further comprises:

applying a fourth current to the fourth pair of electrodes to produce a fourth electrical field;

measuring, using the first pair of electrodes, the second pair of electrodes, and the third pair of electrodes, values associated with the fourth electrical field; and/or.

re-deploying the balloon catheter at a second longitudinal position within the native valve annulus so that the balloon conforms to the surface of the native valve annulus at the second longitudinal position; applying a third current to the first pair of electrodes to produce a third electrical field; measuring, using the second pair of electrodes, values associated with the third electrical field; applying a fourth current to the second pair of electrodes to produce a fourth electrical field; measuring, using the first pair of electrodes, values associated with the fourth electrical field; and determining one or more secondary dimensions of the native valve annulus based at least on the values associated with the third electrical field and the fourth electrical field; and/or obtaining three-dimensional information about the native valve annulus by combining the one or more dimensions of the native valve annulus and the one or more secondary dimensions of the native valve annulus.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A system for determining the dimensions and geometry of a native valve annulus for trans-catheter valve implantation, the system comprising:
   a balloon extending in a longitudinal direction and having an interior surface;
   a shaft extending in the longitudinal direction within the balloon;
   a first pair of electrodes on the interior surface of the balloon and configured to produce a first electrical field based on a first predetermined current;
   a second pair of electrodes on the interior surface of the balloon and configured to produce a second electrical field based on a second predetermined current;
   a first sense electrode pair on the shaft and configured to detect the first and second electrical fields; and
   a second sense electrode pair on the shaft and configured to detect the first and second electrical fields.

2. The system of claim 1, wherein the balloon is an insulative material such that the first electrical field and the second electrical field are confined to an area inside the balloon.

3. The system of claim 1, wherein the first sense electrode pair is at a midpoint of a length of the shaft within the balloon.

4. The system of claim 1, wherein:
   an electrode of the first pair of electrodes is positioned at an angle of about 90° in a circumferential direction of the balloon from an electrode of the second pair of electrodes; and
   the second sense electrode pair is positioned at an angle of about 90° in the circumferential direction of the balloon from the first sense electrode pair.

5. The system of claim 1, further comprising:
   a third pair of electrodes on the shaft, one electrode of the third pair of electrodes being positioned a predetermined distance in a first direction along the shaft from the first sense electrode pair and the other electrode of the third pair of electrodes being positioned the predetermined distance in a second direction along the shaft from the first sense electrode pair, the second direction being opposite the first direction, the third pair of electrodes being configured to produce a third electrical field based on a third predetermined current; and
   a third sense electrode pair on the shaft and configured to detect the third electrical field.

6. A method for determining the dimensions and geometry of a native valve annulus for trans-catheter valve implantation, the method comprising:
   loading a balloon catheter in a delivery system, the balloon catheter comprising:
      a balloon extending in a longitudinal direction and having an interior surface;
      a shaft extending in the longitudinal direction within the balloon;
      a first pair of drive electrodes on the interior surface of the balloon;
      a second pair of drive electrodes on the interior surface of the balloon;
      a first sense electrode pair on the shaft; and
      a second sense electrode pair on the shaft;
   delivering the balloon catheter to the native valve annulus;
   deploying the balloon catheter within the native valve annulus so that the balloon conforms to a surface of the native valve annulus;
   applying a first current to the first pair of electrodes to produce a first electrical field;
   applying a second current to the second pair of electrodes to produce a second electrical field;
   detecting the first electrical field with the first and second sense electrode pair;
   detecting the second electrical field with the first and second sense electrode pair; and
   determining one or more dimensions of the native valve annulus based at least on the detected first electrical field and the detected second electrical field.

7. The method of claim 6, wherein the balloon is an insulative material such that the first electrical field and the second electrical field are confined to an area inside the balloon.

8. The method of claim 6, wherein the first sense electrode pair is at a midpoint of a length of the shaft within the balloon.

9. The method of claim 6, wherein the electrodes that comprise the first and second pairs of drive electrodes are affixed about 180° apart on the interior surface such that the electrodes of the first and the second drive electrode pairs are about 90° degrees apart on the interior surface; and
   the electrodes that comprise the first and sense electrode pairs are affixed about 180° apart on the shaft such that the electrodes of the first and the second sense electrode pairs are about 90° apart on the shaft.

10. The method of claim 6, wherein the balloon catheter further comprises:
    a third pair of electrodes on the shaft, one electrode of the third pair of electrodes being positioned a predetermined distance in a first direction along the shaft from the first sense electrode pair and the other electrode of the third pair of electrodes being positioned the predetermined distance in a second direction along the shaft from the first sense electrode pair, the second direction being opposite the first direction; and
    a third sense electrode pair on the shaft; and
    the method further comprises:
       applying a third current to the third pair of electrodes to produce a third electrical field;
       detecting the third electrical field with the third sense electrode pair; and
       further determining the one or more dimensions of the native valve annulus based at least on the detected third electrical field.

11. A method for determining the dimensions and geometry of a native valve annulus for trans-catheter valve implantation, the method comprising:
    receiving, with one or more processors, first voltage values from a first sense electrode pair on a shaft of a balloon catheter, the first sense electrode pair being configured to detect a first electrical field produced by a first pair of drive electrodes and a second electrical field produced by a second pair of drive electrodes;
    receiving, with the one or more processors, second voltage values from a second sense electrode pair on the shaft of the balloon catheter, the second sense electrode pair being configured to detect the first electrical field and the second electrical field;
    determining, with the one or more processors, a major axis length of the native valve annulus based on the first and second voltage values;

determining, with the one or more processors, a minor axis length of the native valve annulus based on the first and second voltage values; and determining, with the one or more processors, an eccentricity of the native valve annulus based on the determined major axis length and the determined minor axis length.

12. The method of claim 11, further comprising:

determining, with the one or more processors, an estimated major axis length of the native valve annulus by providing the first and second voltage values to a statistical model of the native valve annulus;

wherein the step of determining the major axis length of the native valve annulus includes applying an optimization model of the native valve annulus to the estimated major axis length.

13. The method of claim 11, further comprising:

determining, with the one or more processors, at least one offset value associated with the balloon catheter based on the received first and second voltage values, wherein the at least one offset value identifies an amount of offset of an axis of the balloon catheter relative to an axis of the native valve annulus.

14. A method for determining the dimensions and geometry of a native valve annulus for trans-catheter valve implantation, the method comprising:

loading a balloon catheter in a delivery system, the balloon catheter comprising:
a balloon extending in a longitudinal direction;
a shaft extending in the longitudinal direction within the balloon;
a plurality of splines connected to the shaft;
a first pair of electrodes on a first pair of the splines; and
a second pair of electrodes on a second pair of the splines;

delivering the balloon catheter to the native valve annulus;

deploying the balloon catheter at a first longitudinal position within the native valve annulus so that the balloon conforms to a surface of the native valve annulus at the first longitudinal position;

deploying the plurality of splines so that the splines move radially outward from the shaft;

applying a first current to the first pair of electrodes to produce a first electrical field;

measuring, using the second pair of electrodes, values associated with the first electrical field;

applying a second current to the second pair of electrodes to produce a second electrical field;

measuring, using the first pair of electrodes, values associated with the second electrical field; and determining one or more dimensions of the native valve annulus based at least on the values associated with the first electrical field and the second electrical field.

15. The method of claim 14, wherein the balloon catheter further comprises:
a central ring electrode located on the shaft, and
the method further comprises:
measuring at the central ring electrode values associated with the first electrical field.

16. The method of claim 15, further comprising:
measuring at the central ring electrode values associated with the second electrical field.

17. The method of claim 14, wherein the balloon catheter further comprises:
a third pair of electrodes on a third pair of the plurality of splines; and
the method further comprises:
applying a third current to the third pair of electrodes to produce a third electrical field;
measuring, using the first pair of electrodes and the second pair of electrodes, values associated with the third electrical field.

18. The method of claim 17, wherein the balloon catheter further comprises:
a fourth pair of electrodes on a fourth pair of the plurality of splines; and
the method further comprises:
applying a fourth current to the fourth pair of electrodes to produce a fourth electrical field;
measuring, using the first pair of electrodes, the second pair of electrodes, and the third pair of electrodes, values associated with the fourth electrical field.

19. The method of claim 14, further comprising:
re-deploying the balloon catheter at a second longitudinal position within the native valve annulus so that the balloon conforms to the surface of the native valve annulus at the second longitudinal position;
applying a third current to the first pair of electrodes to produce a third electrical field;
measuring, using the second pair of electrodes, values associated with the third electrical field;
applying a fourth current to the second pair of electrodes to produce a fourth electrical field;
measuring, using the first pair of electrodes, values associated with the fourth electrical field; and
determining one or more secondary dimensions of the native valve annulus based at least on the values associated with the third electrical field and the fourth electrical field.

20. The method of claim 19, further comprising:
obtaining three-dimensional information about the native valve annulus by combining the one or more dimensions of the native valve annulus and the one or more secondary dimensions of the native valve annulus.

* * * * *